United States Patent
Hadden

(10) Patent No.: US 7,153,499 B2
(45) Date of Patent: Dec. 26, 2006

(54) VACCINE IMMUNOTHERAPY FOR IMMUNE SUPPRESSED PATIENTS

(75) Inventor: John W. Hadden, Cold Spring Harbor, NY (US)

(73) Assignee: IRx Therapeutics, Inc., New York, NY (US)

( * ) Notice: Subject to any disclaimer, the term of this patent is extended or adjusted under 35 U.S.C. 154(b) by 0 days.

(21) Appl. No.: 10/430,506

(22) Filed: May 5, 2003

(65) Prior Publication Data

US 2003/0206885 A1 Nov. 6, 2003

Related U.S. Application Data

(63) Continuation of application No. 10/015,123, filed on Oct. 26, 2001.

(60) Provisional application No. 60/243,912, filed on Oct. 27, 2000.

(51) Int. Cl.
*A61K 45/00* (2006.01)

(52) U.S. Cl. .................. 424/85.2; 424/85.1; 424/85.4; 424/85.5; 514/2; 514/110; 514/420

(58) Field of Classification Search ............ 424/85.2, 424/85.1, 85.4, 85.5; 514/2, 110, 420
See application file for complete search history.

(56) References Cited

U.S. PATENT DOCUMENTS

| | | | | |
|---|---|---|---|---|
| 5,098,702 A | * | 3/1992 | Zimmerman et al. | 424/85.1 |
| 5,100,664 A | * | 3/1992 | Doyle et al. | 424/85.2 |
| 5,503,841 A | * | 4/1996 | Doyle et al. | 424/278.1 |
| 5,626,838 A | * | 5/1997 | Cavanaugh, Jr. | 424/54 |
| 5,632,983 A | * | 5/1997 | Hadden | 424/85.1 |
| 5,643,565 A | * | 7/1997 | Doyle et al. | 424/85.2 |
| 5,698,194 A | * | 12/1997 | Hadden | 424/85.1 |
| 5,773,006 A | * | 6/1998 | Anderson et al. | 424/195.11 |
| 5,800,810 A | * | 9/1998 | Doyle et al. | 424/85.2 |
| 5,830,452 A | * | 11/1998 | Bauer et al. | 424/85.2 |
| 6,060,068 A | * | 5/2000 | Doyle et al. | 424/278.1 |
| 2002/0034494 A1 | | 3/2002 | Vicari et al. | |

FOREIGN PATENT DOCUMENTS

EP 0 974 357 A1 7/1998

OTHER PUBLICATIONS

Meneses, Abelardo, et al., "Histologic Findings in Patients with Head and Neck Squamous Cell Carcinoma Receiving Perilymphatic Natural Cytokine Mixture (IRX-2) Prior to Surgery," *Arch Pathol Lab Med*, vol. 122:447-454 (1998).

Hadden, John W. et al., "Interleukins and Contrasuppression Induce Immune Regression of Head and Neck Cancer," *Arch Otolaryngol Head Neck Surg.*, vol. 120:395-403 (1994).

Hadden, J. et al., "A trial of IRX-2 in patents with squamous cell carcinomas of the head and neck," *International Immunopharmacology*, 3:1073-1081 (2003).

Barrera, Jose Luis, et al., "Combination Immunotherapy of Squamous Cell Carcinoma of the Head and Neck," *Archives of Otolaryngology—Head & Neck Surgery*, 126.3:345-351 (2000).

* cited by examiner

*Primary Examiner*—L Blaine Lankford
(74) *Attorney, Agent, or Firm*—Kenneth I. Kohn; Kohn & Associates, PLLC

(57) ABSTRACT

The present invention provides a formulation for inhibiting metastasis which includes 150–600 units of IL-2, a nonsteroidal anti-inflammatory drug (NSAID), and cyclophosphamide. The present invention further provides a formulation for inhibiting metastasis that includes IL-1, IL-2, IL-6, IL-8, δ-IFN and TNF-α.

2 Claims, 10 Drawing Sheets

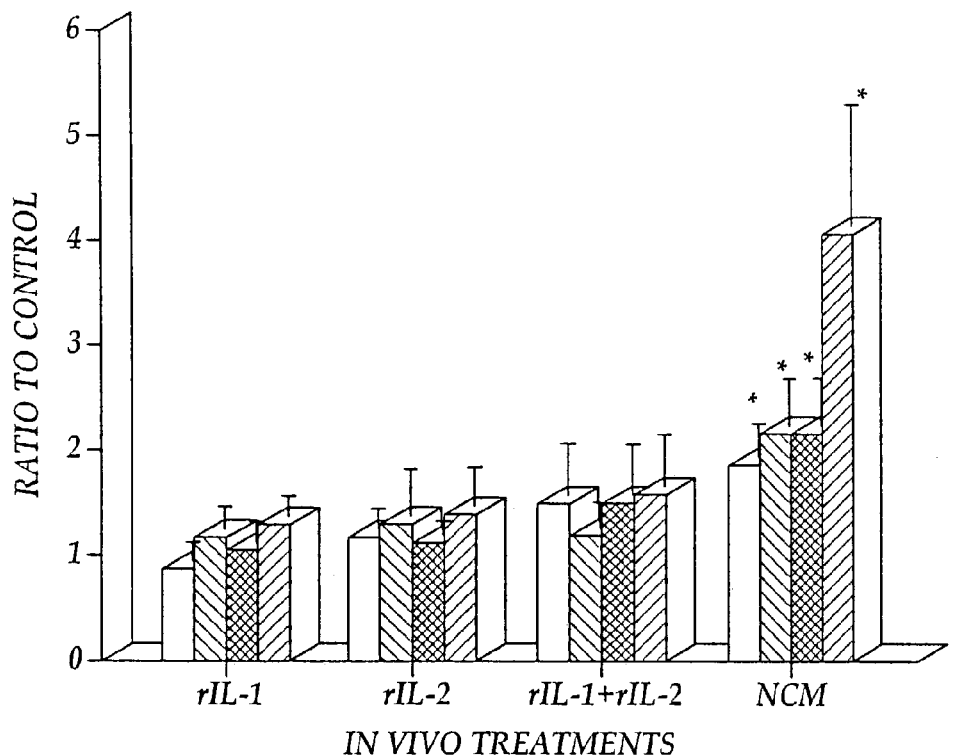
Figure 7
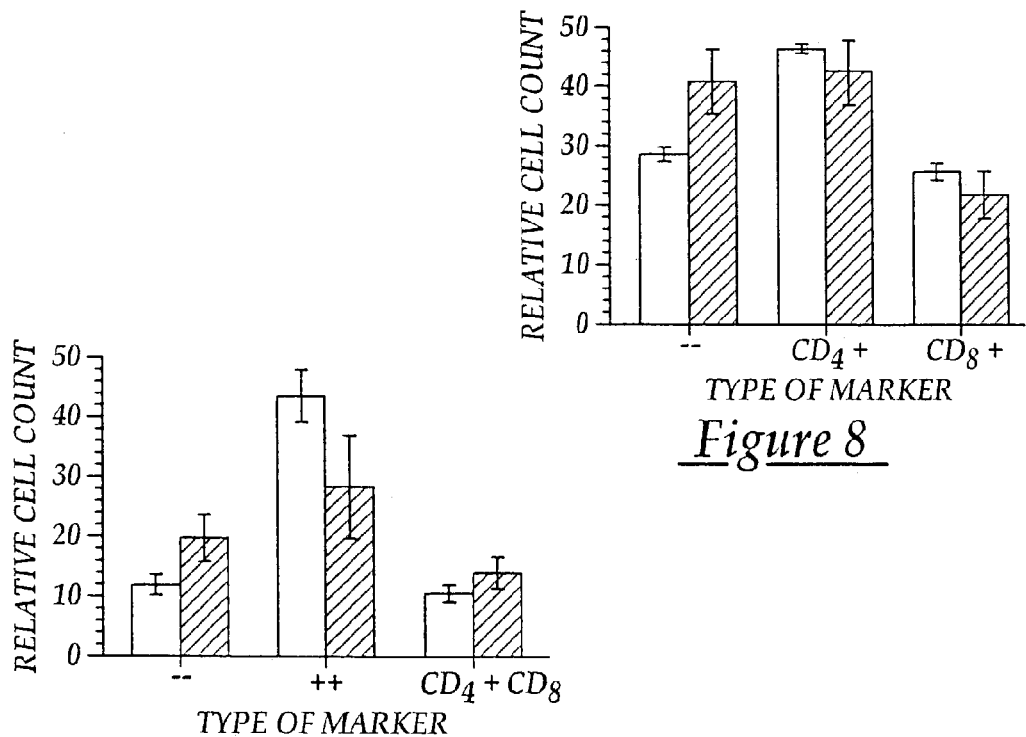
Figure 8
Figure 9

VACCINE IMMUNOTHERAPY FOR IMMUNE SUPPRESSED PATIENTS

CROSS-RELATED REFERENCE SECTION

This application is a Continuation Application of U.S. patent application Ser. No. 10/015,123, filed Oct. 26, 2001, which claims the benefit of priority under 35 U.S.C. Section 119(e) of U.S. Provisional Patent Application No. 60/243,912, filed Oct. 27, 2000, both of which are incorporated herein by reference.

BACKGROUND OF THE INVENTION

1. Technical Field

The present invention relates to vaccine therapy for cancer patients. More specifically, the present invention relates to a vaccine immunotherapy which immunizes cancer patients, having immune suppression, to both endogenous and exogenous tumor peptides or proteins.

2. Background Art

It has become increasingly apparent that human cancers have antigens which, if reacted upon by the host's immune systems, lead to tumor regression. These antigens have been defined by both serological and cellular immune approaches. This has lead to the definition of both B and T cell epitopes (Sahin U, et al, Curr Opin Immunol 9:709–715, 1997; Van der Eynde, B, et al. Curr Opin Immunol 9:684–693, 1997; Wang R F, et al., Immunologic Reviews 170:85–100, 1999). Based upon these results, it has become a goal of cancer immunotherapists to induce regressions of tumors. However, historically, successful efforts have been sporadic and generally minor in frequency and magnitude.

A fundamental problem in the effort to immunize cancer patients is that the tumor-bearing state is associated with immunosuppressive mechanisms derived from both the tumor and the host's disturbed immune system (Kavanaugh D Y, et al, Hematol-Oncol Clinics of North Amer 10(4): 927–951, 1996), thereby making immunization difficult and until now impossible on a consistent basis. Immune suppression or depletion involves a reduced capacity of the immune system to respond. Such suppression can be drug or disease induced. The condition can be drug induced by treatment, virus induced as in AIDS, or induced by a disease state such as cancer. The immune system in this condition is effectively turned off.

A variety of tumor immunization strategies have been developed. However, all of these strategies are complex and deviate significantly from the conventional immunization strategies used for infectious diseases (Weber J. Tumor, Medscape Anthology 3:2, 2000). One such tumor immunization strategy involves Theratope®, a Sialyl $T_N$ polysaccharide mucin antigen conjugated with keyhole limpet hemocyanine and administered with Detox® mycobacterium adjuvant and low dose cyclophosphamide (Maclean G D, et al, J Immunother Emphasis Tumor Immunol 19(4): 309–316, 1996). However, use of this vaccine in patients with metastatic breast and ovarian cancer has yielded major clinical responses in a low percentage of patients. A major response means greater than 50% tumor reduction.

Gene therapy has also been attempted using an adenovirus construct as an expression vector for genes expressing Papilloma virus peptide 16 has been used for immunization or patients with cervical cancer and has yielded major clinical responses in a low percentage of patients (Borysiewickz L K, et al, Lancet 347:1524–1527, 1996).

Dendritic cell mediated therapy has also been attempted, wherein dendritic cells were pulsed with oligopeptide fragments of prostate specific antigens (PSA). Prostate specific membrane antigen (PSMA) has been used in patients with metastatic prostate cancer with major clinical responses in a low percentage of patients (Sanda M G, et al, Urology 52:2, 1999; Murphy G P, et al, The prostate. 38:43–78, 1999)

Additionally, autologous tumors have been, used with low dose cyclophosphamide and BCG to immunize cancer patients with malignant melanoma. However, few clinical responses were reported (Mastrangelo M J, et al, Seminars in Oncology 23(6):773–781, 1996). Another strategy attempted included using MAGE antigens with a variety of vaccine adjuvants. Again, this has yielded few, if any, responses in patients with malignant melanoma (personal communication Thierry Boon).

Several patents to Doyle et al (U.S. Pat. Nos. 5,503,841; 5,800,810; 6,060,068; 5,643,565; 5,100,664) disclose methods of enhancing the immune response in patients using Interleukin 2—(IL-2). This method is disclosed for use in response to infectious diseases and primarily functions using antigens known to be immunogenic. Limited applicability was demonstrated. As disclosed above, the treatment of cancer is known to require different approaches. To date, treatment with IL-2 has shown minor effects in two cancers, renal cell and malignant melanoma (response rates less than 20%). It is generally considered ineffective in squamous cell head and neck and cervical cancer and in prostate cancer. Hence, it is not approved for these uses. It would therefore not be within the skill of one in the art to apply the method of the Doyle et al patents to the use of small peptides in the treatment of cancer.

It is important to contrast prevention with known "classic" antigens of complex structure and high molecular weights in healthy patients vs. treatment (generally unsuccessful) with tumor antigens or peptides (general unsuccessful) in immunosupressed patients (generally unsuccessful). The first is easy and our current viral vaccines attest to their efficacy. The latter is nearly impossible on a routine basis despite 30 years of intense effort.

It is important that this invention relates to, but not exclusively to, immunizing with endogenous peptide processed and presented by dendritic cells or endogenously administered to an environment (lymph node) where dendrtic cells have been prepared and can present them to T-cells effectively. This goal is considered by many immunologists to be insurmountable, Peptides are much too small to be effective immunogens, their one half life is short they are often nonmutated self antigens to which In several of the above strategies, cellular and/or tumoral immunity to tumor-associated antigens has been induced (Weber J. Tumor, Medscape Anthology 3:2, 2000; Maclean G D, et al, J Immunother Emphasis Tumor Immunol 19(4): 309–316, 1996; Borysiewickz L K, et al, Lancet 347: 1524–1527, 1996; Sanda M G, et al, Urology 52:2, 1999). This is especially so in association with tumor regression. Nevertheless, the success rate of such treatments is negligible and inconsistent (<30%).

It would therefore be useful to develop a consistent and effective method of immunizing cancer patients.

SUMMARY OF THE INVENTION

In accordance with the present invention there is provided a formulation for inhibiting metastasis including 150–600 units of IL-2, a nonsteroidal anti-inflammatory drug (NSAID) and cyclophosphamide. Also provided is a formulation for inhibiting metastasis including IL-1, IL-2, IL-6, IL-8, δ-IFN and TNF-α.

BRIEF DESCRIPTION OF THE DRAWINGS

Other advantages of the present invention are readily appreciated as the same becomes better understood by reference to the following detailed description when considered in connection with the accompanying drawings wherein:

FIG. 7 is a graph also showing a comparison of treatment with recombinant IL1, IL2, IL1 plus IL2, and NCM;

FIG. 8 is a graph demonstrating the effect of NCM treatment in vivo on splenocyte and thymocyte markers;

FIG. 9 is a bar graph also demonstrating the effect of NCM treatment in vivo on splenocyte and thymocyte markers;

DESCRIPTION OF THE INVENTION

Figure 1:
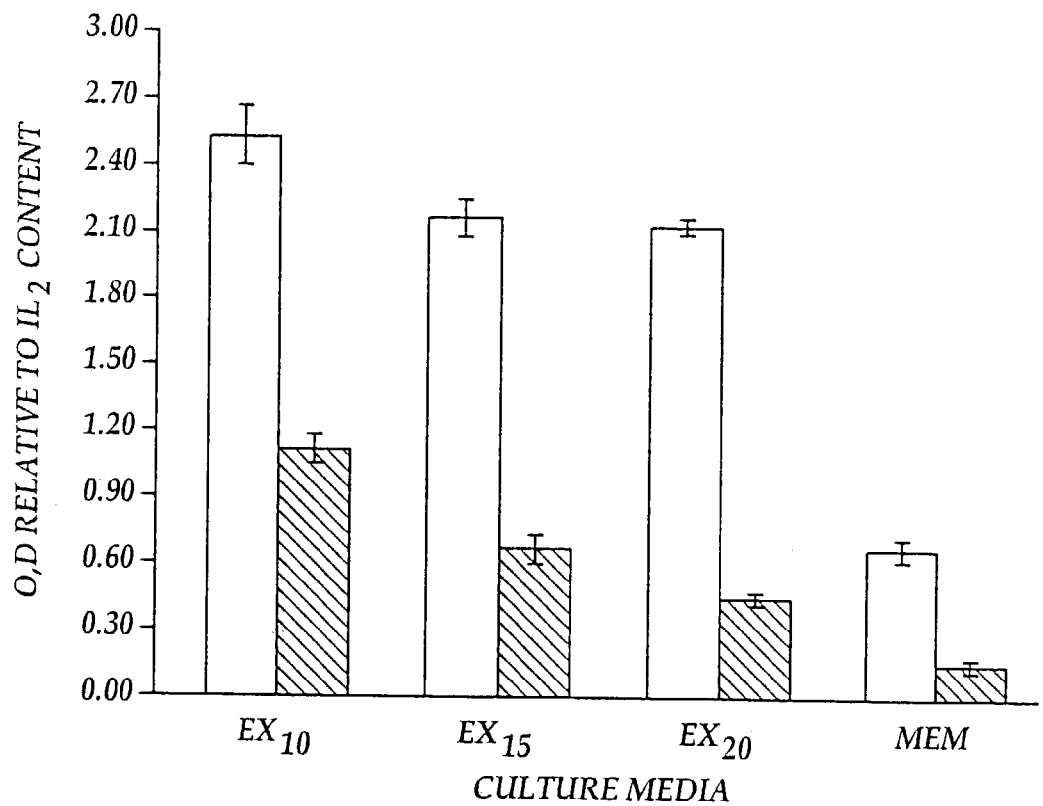
FIG. 1 is a graph showing a comparison of NCM in different media utilizing continuous versus pulsed exposure to PHA.

Generally, the present invention provides methods for treating patients utilizing vaccine immunotherapy wherein the patients are immune suppressed. By immune suppressed, it is meant that the patient has reduced cellular immunity and thus impaired capacity to respond to new antigens. More specifically, in blood, T lymphocyte counts are reduced and/or function of these cells is impaired, as shown, e.g. by PHA proliferation assay.

T lymphocytopenia (low T cell levels in blood) is a diagnostic characteristic of cellular immune deficiency; impaired function of existing thymphocytes is the other characteristic. There is no generally accepted (clinically approved) way to treat T lymphocytopenia. Bone marrow transplants (± thymus transplants) have been used in cases of severe combined immunodeficiency (SCID—congenital, irradiation or chemotherapy induced). Recombinant IL2 has been tried in AIDS with some effect by much toxicity.

There are two ways to make new T cells to attempt to correct T lymphocytopenia. One way, as in rIL-2 therapy, expands T cells already in the periphery, i.e., memory T cells ($CD_{45}RO$) (blood, lymph node and spleen). The other involves processing in the thymus of new T cells from bone marrow—derived precursors. This happens naturally in children but not in adults. These new cells are called recent "thymic émigrés" and have the surface marker of "naïve" T cells i.e., $CD_{45}RA$. NCM therapy (plus Thymosin $\alpha_1$) results in the production of these new T cells as well as expanding preexisting memory T cells.

More specifically, the present invention utilizes new discoveries relating to immunization to provide an immune response to antigens which is either endogenously or exogenously administered. Such antigens in the past may have been believed to be immunogenic while others used in the present invention may have been thought previously to be non-immunogenic. Examples of such antigens are EADPT-GHSY (melanoma) from MAGE-1 protein, EVDPIGHLY (lung carcinoma) from MAGE-3, EVDPIGHLY (lung carcinoma) from MAGE-3, and many others. (See Bellone, et al, Immunology Today, Vol 20, No. 10, p 457–462, 1999.)

The present invention utilizes several general newly derived method steps for obtaining immunization in subjects where such immunization was previously thought to be impossible. More specifically, the present invention provides a method for overcoming immune depression by inducing production of naïve T cells. The term "naïve" T cells is meant to mean newly produced T cells, even in adults, wherein these T cells have not yet been exposed to antigen. Such T cells at this stage are non-specific yet capable of becoming specific upon presentation by a mature dendritic cell having antigen, such as tumor peptides, exposed thereon. Thus, the present invention replenishes or generates new T cells. This is generally accomplished by administering a natural cytokine mixture (NCM). The NCM includes IL1, IL2, IL6, IL8, IL10, IL12, δIFN, TNFα and G- and GM-CSF. The amount and proportions of these constituents are detailed below. Preferably, about 150–600 units of IL2 are contained in the NCM.

Preferably, the NCM is injected around lymphatics that drain into lymph nodes regional to a lesion, such as a tumor or other persistent lesions being treated. Perilymphatic administration into the lymphatics which drain into the lymph nodes, regional to the lesion, such as a cancer, is critical. Peritumoral injection has been associated with little response, even progression and is thus contraindicated. A ten (10) day injection scheme is optimal and a twenty (20) day injection protocol, while effective clinically, tends to reduce the TH1 response and shift towards a less desirable TH2 response as measured by lymphoid infiltration into the cancer. Bilateral injections are effective. Where radical neck dissection has occurred, contralateral injection is effective.

It is preferable to block endogenous suppression of T cells, such as caused by various cancer lesions. Blocking is effected by the codelivery of low dose cyclophosphamide and a non-steroidal anti-inflammatory drug (NSAID). The NSAID of choice is indomethacin. While indomethacin is the most effective NSAID, it is also arguably the most toxic. Celebrex® and Vioxx®, Cox II NSAIDS, are less effective. Vioxx® can be more toxic, causing gastritis in many patients. Ibuprophen was effective but the histological responses were characteristic of a TH2 rather than TH1 mediated response, this being less desirable. Side effects of NSAIDS are to be aggressively treated with proton inhibitors and a prostaglandin E analog. Zinc and multi-vitamins are useful agents to help restore T cell immunity. Applicants have found that treatment with contrasuppression and zinc without the NCM is ineffective.

In summary, the minimum regimen is perilymphatic treatment with the NCM combined with contrasuppression using cyclophosphamide and an NSAID. The alternative regimen is the previously mentioned regimen further including zinc and vitamins, possibly including the addition of selenium. Preferable dosing of Zinc is 50 to 75 mg. A standard multivitamin can be administered. The zinc can be an available gluconate.

In order to maximize clinical response and for the greatest increase in survival rate, the degree and type of lymphocyte infiltration is important. Lymphocyte: granulocyte or macrophage infiltration of a 90:10 ratio is optimal. T and/or B cell infiltration preferably is diffuse and intense and not peripheral. Light infiltration of less than 20% is not associate with a robust clinical response. Tumor reduction and fragmentation in the histological samples is preferred in reflecting a good response.

Lymph node changes key to good response involve at least five (5) aspects. Lymph node enlargement and not just reversal of tumor induced reduction of size but overall increase in size compared to normal is preferred. Increased T and B cell areas indicate an immunization. Sinus histocytosis (SH) is believed to be the accumulation of immature dendritic cells which have ingested and processed tumor antigens but are unable to mature and present these tumor peptides to naïve T cells capable of stimulating TH1 and TH2 effective cells which lead to cytotoxin T cell and B cells. Reversal of SH is preferred Thus, the present invention provides for unblocking immunization at a regional lymph node by promoting differentiation and maturation of immature dendritic cells in a regional lymph node and thus allowing presentation by resulting mature dendritic cells of small peptides, generally nine amino acids in length to T cells to gain immunization of the T cells. Additionally, induction of mature dendritic cells is required. Finally, mobilization of peripheral blood T-lymphocytes in T-lymphocytopoenic patients in the presence of induction of naïve T cells capable of responding to dendritic cells presenting endogenous tumor peptides is desired. (See Sprent, et al, Science, Vol 293, Jul. 13, 2001, pgs 245–248).

In view of the above, the key mechanistic features of the present invention are the in vivo maturation of dendritic cells resulting in effective peptide antigen presentation. Based on the examples presented below, increases in CD45 RA positive naïve uncommitted T cells have been found. With antigen, this leads to T and B cell clonal expansion, creating immunity in the patient. The resulting infiltration into tumors by hematogenous spread leads to robust tumor destruction. The result, as found in the data below, is increased survival due to immunologic memory. (See Sprent et al, cited above).

It is predicted logically that exogenously provided synthetic or extracted tumor peptides (See Bellone, et al, cited above) can be delivered into the pre-primed or co-primed regional or distal lymph node and yield tumor antigen specific T cells, with or without B cells. Three examples are set forth below. In view of the above, it can be concluded that the action of NCM plus other agents is useful as for any tumor antigens (synthetic and endogenous, peptides and proteins). Many of these peptides are not normally immunogenic and only when presented by a matured, activated dendritic cell, will they be effective in immunizing naïve T cells. Thus, the appearance of an immune T cell means, de facto, that a dendritic cell has been made or allowed to work properly. Also de facto, dendritic cell activation and maturation is to be considered a key factor in cancer immunodeficiency as well as the well-known defects in T cells such as a decreased number and function with anergy and presumed apoptosis.

Referring more specifically to the protocol and medicant delivered in accordance with the present invention, the invention utilizes the natural cytokine mixture (NCM) to immunize patients, such as cancer patients, as well as patients with other lesions or antigen producing disease conditions. More specifically, the present invention utilizes a method of enhancing the immune response of cancer patients to a cancer by administering an effective amount of a composition containing therein the NCM and a tumor-associated antigen, the NCM acting as an adjuvant to produce the immune response. The tumor associated antigen can be either an endogenously processed tumor peptide preparation resident in regional nodes of patients with cancer or in conjunction with an exogenously administered tumor antigen preparation in or near these nodes. Tumor peptides, as well as antigens, are included herein even though peptides are not expected to be immunogenic where tumor associated protein antigens would more likely be more so since they are complete.

In the preferred embodiment, the composition of the present invention involves the administration of the NCM plus a tumor associated or specific antigen, as defined below with low doses of cyclophosphamide, a cyclooxygenase inhibitor, and other similar compounds which have been shown to further increase the effects of the composition of the present invention.

To clarify and further define the above, the following definitions are provided. By "adjuvant" it is meant a composition with the ability to enhance the immune response to a particular antigen. To be effective, an adjuvant must be delivered at or near the site of antigen. Such ability is manifested by a significant increase in immune mediated protection. Enhancement of immunity is typically manifested by a significant increase (usually greater than 10 fold) in the titer of antibody raised to the antigen. Enhancement of cellular immunity can be measured by a positive skin test, cytotoxic T-cell assay, ELISPOT assay for δIFN or IL-2, or T-cell infiltration into the tumor (as described below).

By "tumor associated antigen", it is meant an analogous protein or peptide (which were previously shown to work by pulsing of dendritic cell ex vivo) or other equivalent antigen. This can include, but is not limited to PSMA peptides, MAGE peptides (Sahin U, et al, Curr Opin Immunol 9:709–715, 1997; Wang R F, et al, Immunologic Reviews 170:85–100, 1999), Papilloma virus peptides (E6 and E7), MAGE fragments, NY ESO-1 or other similar antigens.

Previously, these antigens were not considered to be effective in treating patients based either on their size, i.e. they are too small or that they were previously thought to not have the immunogenic properties (i.e., self antigens).

NCM, a non-recombinant cytokine mixture, is defined as set forth in U.S. Pat. Nos. 5,632,983 and 5,698,194. Briefly, NCM is prepared in the continuous presence of a 4-aminoquinolone antibiotics and with the continuous or pulsed presence of a mitogen which in the preferred embodiment is PHA.

According to the present invention, there is provided a partially characterized NCM that has been previously shown to be effective in promoting T cell development and function in aged, immunosuppressed mice. Upon administering this NCM to immunosuppressed patients with head and neck cancer, it is demonstrated in this application for the first time that the mobilization of T lymphocytes in the blood of cancer patients treated with the NCM produces an increase in immature, naïve T cells bearing both CD2 and CD45 RA. This is one of the first demonstrations that adult humans can generate naïve T cells. Previous references: Mackall et al, (New England Journal of Medicine (1995), Vol. 332, pp. 143–149); and a review by Mackall (Stem Cells 2000, Vol. 18, pp. 10–18) discusses the inability to generate new T cells in adults but not children, and discusses the problem of trying to replenish T cells following cancer chemotherapy and/or radiotherapy. In general there is the dogma that new T cells are not generated in the adult human. However, following bone marrow transplantation for intense chemotherapy, there has been evidence that new T cells can be generated in the adult. No molecular therapy to date has been able to achieve this, although increase in lymphocytes counts have been achieved with prolonged and intense therapy with recombinant interleukin-2 in patients infected by HIV. These have not been clearly demonstrated to be thymus derived T cells and are presumably an expansion of pre-existing peripheral T cells.

Previously, Cortesina et al. employed a natural IL-2, perilymphatically in patients with head and neck cancer and induced several tumor regressions (Cortesina G, et al, Cancer 62:2482–2485, 1988) with some tumor infiltration with leukocytes (Valente G, et al, Modern Pathol 3(6):702–708, 1990). Untreatable recurrences occurred and the response was termed non-specific and without memory and thus nonimmunologic (Cortesina G, et al, Br J Cancer 69:572–577, 1994). The repeated attempts to confirm the initial observations with recombinant IL-2 were substantially unsuccessful (Hadden J W, Int'l J Immunopharmacol 11/12:629–644, 1997).

The method of the present invention involves using NCM with local perilymphatic injections or other injections that are known to those of skill in the art to provide sufficient localization of the immunotherapy compound. In the preferred embodiment, the injections take place in the neck, but can be applied in other locations as required by the disease to be treated. This treatment induced clinical regressions in a high percentage of patients who also showed improved, recurrence free survival (Hadden J W, et al, Arch Otolaryngol Head Neck Surg. 120:395–403, 1994; Meneses A, et al, Arch Pathol Lab Med 122:447–454, 1998; Barrera J, et al, Arch Otolaryngol Head Neck Surg 126:345–351, 2000; Whiteside, et al, Cancer Res. 53:5654–5662, 1993). Whiteside, et al (Cancer Res. 53:5654–5662, 1993) observed that in head and neck cancer, tumoral injection of recombinant interleukin-2 produced a T cell lymphocyte infiltrate, but without significant clinical responses. Peritumoral injection of Multikine (Celsci Website) (in combination with perilymphatic injection in up to 150 patients resulted in significant tumor responses, i.e. greater than 50% tumor reduction in only 11 patients, making their response rate less than 10% in contrast to the high degree of response observed in the present studies, 40%. In addition, they noted 50% non-responders where Applicants have observed only 20%.

Applicants, have observed that peritumoral and intratumoral injection can be associated with progression of disease even in patients who initially have had a positive response to the NCM protocol, thus undoing its benefit. Peritumoral injection is thus contraindicated and is excluded as part of the present invention. This has led Applicants to the interpretation that the tumor is not the site of immunization and the present application presents documentation that the regional lymph node is the site of immunization. Then, unpublished analysis of regional lymph nodes revealed data which indicated that the regional lymph node is the site of immunization to postulated tumor antigens (FIGS. 14–18). With the identification of a number of different tumor antigens, it has been a conundrum over the last decade that given the presence of such antigens, they have not been employed effectively in immunization protocols. Sporadic positive examples have been reported, but in the main, the data are negative. The problem of antigen presentation has been focused on in the last decade and the dendritic cell has emerged as a critical player in the presentation of small peptides derived from tumors. See DeLaugh and Lotts, Current Opinion In Immunology, 2000, Vol. 12, pp.583–588; Banchereau et al, Annual Reviews of Immunology, (2000), Vol. 18, pp. 767–811; also Albert et al, Nature, Vol. 392, pp.86–89 (1998).

In brief, in order for tumor antigens to be properly antigenic, they must arrive from an apoptotic rather than a necrotic tumor cell (Albert, Nature, 392:86–87, 1997). They need to be captured by immature dendritic cells that have the morphology of large histocytes. These immature dendritic cells process antigen (endocytosis, phagocytosis and digestion) and evolve into mature dendritic cells which display peptide fragments (generally nine amino acids) of the digested antigen in the MHC groove for presentation to T cells. T cells, in order to respond, must have antigen presented to them in the MHC groove plus various co-stimulatory signals. References: Banchereau and DeLaugh.

Investigators, such as Murphy et al, 1999, have utilized dendritic cells generated in culture and then pulsed with tumor antigens and have achieved a small degree of success in immunizing patients against prostate specific membrane antigen peptides. Unfortunately, this approach of pulsing dendritic cells is cumbersome and has been rather inefficient. In the present invention, Applicants have shown that the cells present in the lymph node sinuses, which accumulate in cancer, are cells of the lineage of dendritic cells and that following the in vivo treatment with the NCM protocol, these cells disappear and antigen ultimately then becomes immunogenic for T cells. They are able then to respond to the tumor. So a critical aspect of this invention is being able to generate a microenvironment in the regional lymph node which allows effective antigen processing and presentation. The immunization which derives results in T cells able to traffic to the lesion and destroy tumors is de facto demonstration of adequate antigen processing by dendritic cells. Additionally, none of the patients treated with NCM developed distant metastasis which is expected in up to 15% clinically and up to 50% pathologically. This indicates that a systemic immunity rather than merely a local immunity has been induced by the treatment. This is a drastic improvement over the compositions in the prior art, because the prior art compositions, at best, were inconsistently effective against metastatic disease. The ability of the composition of the present invention to create systemic immunity allows more effective and efficient treatment of a patient. Further, the magnitude of systemic response enables an individual to be administered smaller doses without limiting the effectiveness of the treatment and without toxicity.

The literature (Hadden J W, Int'l J Immunopharmacol 11/12:629–644, 1997; Hadden J W. Immunology and immunotherapy of breast cancer: An update: Int'l J Immunopharmacol 21:79–101, 1999) has indicated that for both SCC and adenocarcinomas, the two major types of cancer, regional lymph nodes reflect abnormalities related to the tumor, including sinus histocytosis, lymphoid depletion and often the presence of anergic tumor associated lymphocytes (capable of reacting to tumor cells with ex vivo expansion and recovery using IL-2). Then, with metastases, lymphoid depletion and depressed function occur. Additionally, uninvolved cervical lymph nodes of such patients have shown a reduction in average size and an increase in sinus histocytosis associated with head and neck cancers. (See FIGS. 14–17).

Specifically relating to the composition, the composition of the present invention involves the natural cytokine mixture plus either endogenous or exogenous tumor associated antigen. Additionally, low doses of cyclophosphamide, cyclooxygenase inhibitors, zinc, and other similar compounds have been shown to further increase the effects of the composition of the present invention.

Immunization for treatment of patients with cellular immune deficiencies associated with cancer, HIV infection, aging, renal transplants and other such deficiencies can be achieved with the composition of the present invention.

Administration and protocols for treatment as follows:

Delivery of Gene Products/synthetic Antigens with:

The compounds of the present invention (including NCM), and exogenous antigens are administered and dosed to achieve optimal immunization, taking into account the clinical condition of the individual patient, the site and method of administration, scheduling of administration, patient age, sex, body weight. The pharmaceutically "effective amount" for purposes herein is thus determined by such considerations as are known in the art. The amount must be effective to achieve immunization including but not limited to improved tumor reduction, fragmentation and infiltration, survival rate or more rapid recovery, or improvement or elimination of symptoms.

In the method of the present invention, the compounds of the present invention can be administered in various ways. It should be noted that they can be administered as the compound or as pharmaceutically acceptable salt and can be administered alone or as an active ingredient in combination with pharmaceutically acceptable carriers, diluents, adjuvants and vehicles. The compounds can be administered intra or subcutaneously, or peri or intralymphatically, intranodally or intrasplenically or intramuscularly, intraperitoneally, and intrathorasically. Implants of the compounds can also be useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days.

When administering the compound of the present invention, it is generally formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Peptides may be polymerized or conjugated to carriers such as human serum albumen as is well known in the art.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicle, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The foregoing provides a protocol for using NCM as an adjuvant to immunize cancer patients against tumor antigens, either autologous or as defined proteins or peptides.

| | The antigen preparations to be used: | In Cancer: |
|---|---|---|
| 1) | PSMA peptides (9) - obtained commercially | Prostate |
| 2) | MAGE 1 & 3 & MAGE fragments & NY ESO-1 obtained from the Ludwig Inst. Of Immunol. | Melanoma, H&NSCC |
| 3) | Papilloma virus E6 & E7 obtained commercially | Cervical SCC |

The commercially route of antigen administration is preferentially the neck because it is accessible and it contains >30% of the bodies lymph nodes and systemic immunity can be envisioned to result.

Low dose cyclosphosphamide: Low dose CY has been used to augment cellular immunity and decrease suppression by lymphocytes in mice and patients with cancer (Berd D., Progress in Clin Biol Res 288:449–458, 1989; Berd D, et al, Cancer Research 47:3317–3321, 1987) and it has been employed in effective immunotherapy of cancer patients (Weber J., Medscape Anthology 3:2, 2000; Murphy G P, Tjoa B A, Simmons S J. The prostate. 38:43–78, 1999; Hadden J W, et al, Arch Otolaryngol Head Neck Surg. 120:395–403, 1994).

Zinc: Zinc deficiency is associated with improved cellular immunity and treatment with zinc is immunorestorative in mice (Hadden J W., Int'l J Immunopharmacol 17:696–701, 1995; Saha A., et al. Int'l J Immunopharmacol 17:729–734, 1995).

A cyclooxygenase inhibitor (COXi) like indomethacin: Cancers produce prostaglandins and induce host macrophage production of prostaglandins (Hadden J W. The immunopharmacology of head and neck cancer: An update. Int'l J Immunopharmacol 11/12:629–644, 1997). Since prostaglandins are known to be immunosuppressive for T cells, inhibition of PG synthesis with cyclooxygenase inhibitors is appropriate.

Recombinant Protein Purification

Marshak et al, "Strategies for Protein Purification and Characterization. A laboratory course manual." CSHL Press, 1996.

Dose and Frequency of Antigens

1–1000 μg, preferably 10–500; form—soluble (partially polymerized or conjugated to carrier, if necessary)
Schedule: Day 1, Day 12, Day 21
(Pre-Rx) Day 12, Day 21, Day 31
Site of injection: local injection, ie. neck injections
Expected Responses: Tumor reduction
  Tumor pathological changes (reduction, fragmentation, lymphoid infiltration)
  Humoral immunity to antigen (RAI or ELISA)
  Cellular immunity to antigen (intracutaneous skin test in vitro lymphocyte proliferation, of ELISPOT ASSAY)

Keep in mind that oligopeptides like PSMA, MAGE fragments, E6, E7 peptides would be poorly immunogenic even pulsing on to dendritic cells. Thus effective immunization would not be expected to occur. Even with effective immunization, tumor regression would be considered surprising by this method, particularly at a distance as with prostate and cervix. Regression of metastastic disease is always a surprising event with immunotherapy. Degree and frequency of clinical responses are a factor in the effectiveness and thus the novelty of this approach.

Diagnostic skin tests are another way to guide us to more effective immunization. Patients can be pretreated with IRX-2 (NCM) to induce better responses (increase NCM and PHA skin tests and lymphocyte counts and reversal of lymph node abnormalities).

This creates an Adjuvant strategy
  Combining immunorestoration and adjuvancy
  Making peptides and proteins immunogenic
  Getting the degree of immune response to effect tumor regression at a distance.
  It can extend to all forms of tumor antigens and haptens including peptides and/or carbohydrates
  It can extend to areas of applicability as in AIDS virus vaccine in HIV+ patients; other difficult to manage situations; renal transplants, aged, etc.

Patients will be skin tested for one or more tumor peptide prior to consideration of the protocol, 100 μg of one or more tumor peptides will be perilymphatically administered in the neck with NCM using the NCM protocol as discussed below on day 1 and 10 of the NCM series. The combination will be repeated on day 21. In addition to tumor response and histology, immune reaction to the peptides will be monitored by repeat skin test or by other means known in the art.

EXAMPLE 1

All steps relating to cell culture are performed under sterile conditions. General methods of cellular immunology not described herein are performed as described in general references for Cellular immunology techniques such as Mishell and Shiigi (Selected Methods in Cellular Immunology, 1981) and as are known in the art.

Preparation of Natural Cytokine Mixture (NCM)

The buffy coat white cells of human blood from multiple HIV-negative hepatitis virus-negative donors is collected. In an alternative embodiment, animals could be the cell source for veterinary uses. The cells from the donors are pooled and layered on ficoll hypaque gradients (Pharmacia) to yield lymphocytes free of neutrophils and erythrocytes. Alternative methods could be used that would result in the same starting lymphocyte population as are known in the art.

The lymphocytes are washed and distributed in X vivo-10 media (Whittaker Bioproducts) to surface activated cell culture flasks for selection of cell subsets MICROCELLECTOR™. T-25 Cell Culture Flasks) in which are immobilized stimulants, i.e. mitogens like PHA. In one set of experiments, X vivo-15 and X vivo-20 media were used as indicated. The immobilization process for the stimulants is as described by the manufacturer for immobilizing various substances for panning procedures, i.e. separating cells, in the flasks. Alternatively, the lymphocytes are exposed to stimulants e.g. PHA for 2–4 hours then washed three times.

The cells are incubated for 24–48 hours in X vivo-10 media with 80 μg/ml ciprofloxacin (Miles Lab) at 37° in a $CO_2$/air incubator. Alternatively, RPMI 1640 media could be used (Webb et al. 1973). Generally the HSA is used at 0.1 to 0.5% (weight by volume). Following incubation the supernatants are poured off and collected. Human serum albumin (HSA) may be added to stabilize further the interleukins if HSA-free media is used for generations. The supernatants are stored at 4° C. to −70°

Characterization of Supernatants

The pooled supernatants are characterized by measuring the cytokine content by bioassay for IL-2 and ELISAs for the remaining interleukins IL-1-IL-15, CSFs, TNFs, and IFNs. Sterility is tested by culture in thioglycolate broth and endotoxin measured by limulus lysate assay as is known in the art.

Standardization of supernatant for cytokine content:

Each supernatant is standardized either by concentration or amount administered so that comparisons can be made.

Removal of contaminants from supernatant:

DNA and virus exclusion, if used, employ such techniques as ultrafiltration, column chromatography, virus retentive filters, ethanol fractionation, polyethylene glycol/bentonite precipitation, gamma irradiation, and/or solvent/detergent treatment as has been used for intravenous gamma globulin and monoclonal antibodies (e.g. IGIV News Update brochure).

Model

The model of hydrocortisone induced thymic involution in aged mice was used unless otherwise indicated (Hadden J W, et al, Int'l J Immunopharmacol 17:821–828. 1995).

Laboratory Animals

Female BALB/c (Life Science, St. Petersburg, Fla.) aged retired breeder mice (8–9 months) whose thymuses had begun to involute were employed in in vivo tests. Mice were weight matched and randomly pooled in groups of five. Animals were fed standard laboratory diets with drinking water ad lib. All mice, with exception of a control group, were treated intraperitoneally (i.p.) with hydrocortisone (5 mg/mouse in 0.1 ml 0.9% sodium chloride) for two consecutive days to induce a chemical thymectomy and reduction of spleen weight.

Hydrocortisone-treated adult mice show acute thymic involution (less than 30% of control) and reduction in spleen size (less than 80% of control) at two days with progressive recovery to 10 days.

Experimental Design

Each treatment group had five (5) animals and each experiment was repeated 2–5 times. Treatment was initiated intraperitoneally (i.p.) on Day 3 and continued once per day for a total of five (5) days. Treatment groups were injected with one of the following in vivo treatments as indicated in the text:

1. pyrogen free saline (controls);
2. recombinant interleukin-1 (rIL-1; 4 ng);
3. recombinant interleukin-2 (rIL-2; 50 units);
4. rIL-1+rIL-2 (4 ng+50 units, respectively)
5. natural cytokine mixture (NCM; 50 units IL-2 equivalence)

On day 8, the mice were weighed, sacrificed by cervical dislocation, and their spleens and thymuses removed and weighed. The organs were minced, the residual erythrocytes were lysed using ammonium chloride (Mishell and Shiigi 1981), and the cells counted.

The proliferative response of the cells to various substances was then determined. A sample of cells was prepared for cell culture at 37° C., 5% $CO_2$ in RPMI 1640 medium with 5% fetal bovine serum, penicillin (100 U/ml), streptomycin (100 µg/ml) and 2-mercaptoethanol ($2 \times 10^{-5}$ M). The cells were plated in 0.2 ml microwell plates in quadruplicate at a concentration of $1.5 \times 10^6$/ml and incubated for 72 hours with one of the following as indicated in the text:

1. control diluent (complete RPMI 1640 medium);
2. rIL-1 (1 ng/ml);
3. rIL-2 (2 Units/ml);
4. NCM (2 Units/ml of IL-2 equivalence)
5. concanavalin A (Con A; 1.5 µg/ml)
6. phytohemagglutinin (PHA; 0.5 µg/ml)

The culture was terminated to measure DNA synthesis, thus cell proliferation, with an 18 hours pulse of tritiated thymidine (3H-Thymidine; New England Nuclear, Boston, Mass.; specific activity 6.7 Ci/mM), harvested with a multiple automatic sample harvester and processed for liquid scintillation counting. Marker studies were also performed as described by, Hadden et al. (1992). The results were expressed as arithmetic mean of cpm from three samples for each animal. In order to simplify the representation of data obtained with different animals, the results with the different animals were pooled and calculated together and in some cases are expressed as ratio to control and others as means+ brackets for standard error of the mean (SEM).

Statistical Analysis

Student's T test was used to analyze data as appropriate.

Results:

The objective was to find a way to stimulate lymphocytes to produce high levels of interleukin-2 in the absence of serum and in a way which did not yield significant quantities of PHA in the supernatant. To do this, the PHA was immobilized on surface activated cell culture flasks for selection of cell subsets (AIS MICROCELLECTOR™. T-25 plates) as described in the manufacturer's instructions for "panning" cell separation or pulsed into the cells followed by washing (pulse technique).

Media employed in these experiments was X vivo-10 (Whittaker) and is approved for administration to humans by the U.S. Food and Drug Administration for interleukin-2-lymphokine activated killer (LAK) cell protocols. Serum-free media capable of supporting human lymphocyte proliferation like minimal essential media (MEM) or RPMI-1640 (Sigma) could also be used.

Initial experiments indicated that PHA (HA-16, Murex Diagnostics Ltd., Dartford, U.K.) could be immobilized by the technique described by the manufacturer and that under appropriate optimal conditions of cell number of $7.5–15 \times 10^6$/ml, time of exposure of 24 hours–48 hours, and PHA concentration of 25 or 50 µg/ml a high yield of interleukin-2 in the serum-free supernatant could be obtained. The yield was superior to the pulse technique employing brief exposures to PHA (NI) followed by washing and subsequent culture with ciprofloxacin (NIM) in serum-free media (Table 1).

TABLE I

| IL content of supernatant/ml | |
|---|---|
| PHA brief exposure(NI) | 2–20 units |
| PHA brief exposure & ciprofloxacin (NIM) | 8–140 units (80 µg/ml) |
| PHA flask immobilization & ciprofloxacin | 100–353 units (80 µg/ml) |

IL-2 content was measured in the supernatant using the CTLL IL-2 dependent cell line by the methods described by Gillis et al. (1978). IL-2 was quantitated in international units against a known standard containing 640 units (Pharmacia AB).

Figure 2:
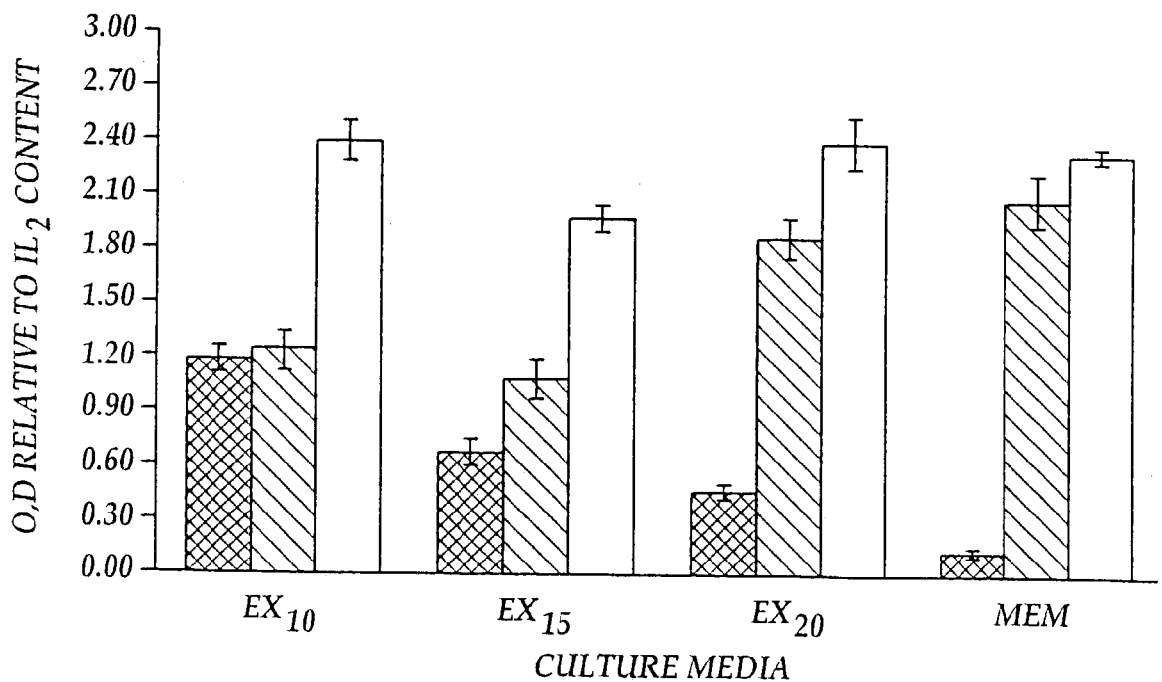
FIG. 2 is a graph showing the effect of cell concentration with continuous exposure to PHA.
Figure 3:
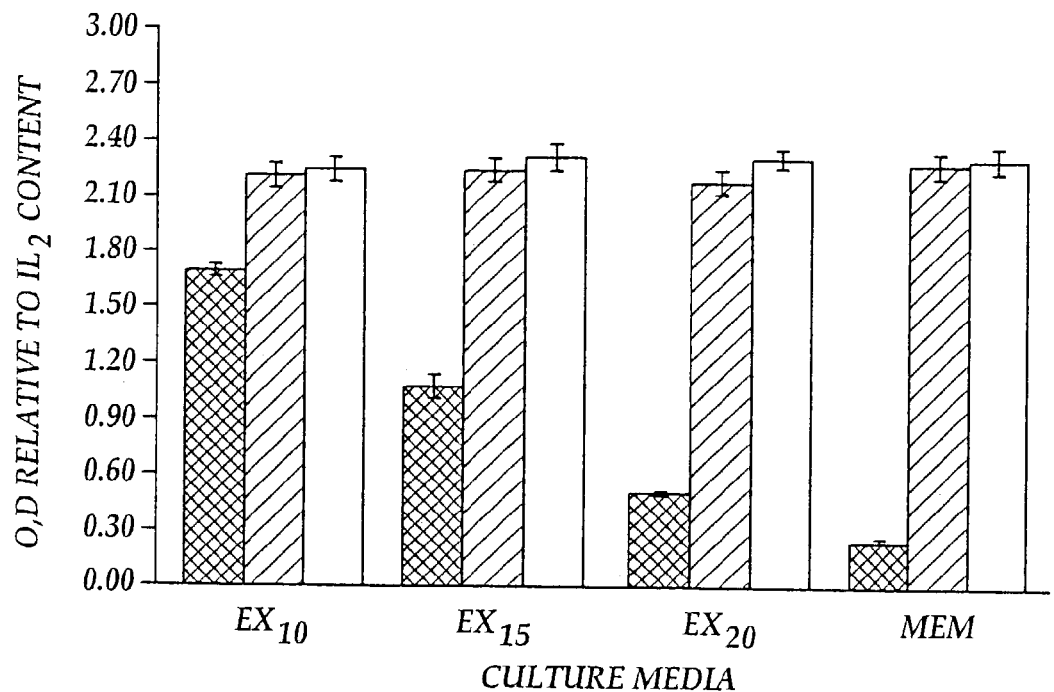
FIG. 3 is a bar graph similar to FIG. 1 with PHA at twice the concentration (2 micrograms per ml)

The cell free supernatants from flasks incubated without cells were tested on human lymphocytes to determine if residual PHA was present in sufficient quantities to produce a proliferative response. Any residual PHA greater than 0.01 µg/ml would give such a response. In the absence of cells, small amounts of PHA were observed in the supernatant at 40–48 hours; however, when PHA (25 µg/ml) was used for only 24 hours, these levels were negligible. 24 hours incubation was thus considered optimal. A comparison of X vivo-10, X vivo-15 and X vivo-20 (Whittaker) and MEM in the present invention was undertaken and shown in FIGS. 1–3. X vivo-10 and X vivo-15; are approved for administration to humans by the U.S. Food and Drug Administration for interleukin-2-lymphokine activated killer (LAK) cell protocols. Generation of NCM was compared in different media utilizing continuous vs. pulsed exposure to PHA at 1 µg/ml (FIG. 1). The effect of cell concentration was explored with continuous exposure to PHA at 1 µg/ml (FIG. 2) and PHA at 2 µg/ml (FIG. 3). The optimal combination of these factors was found to be continuous exposure by immobilization in X-vivo-10 at cell concentrations of 2.5 or $5.0 \times 10^6$/ml with PHA at 2 µg/ml or at $5 \times 10^6$ cells/ml with PHA at 1

μg/ml. Because the per cell yield is most efficient at $2.5 \times 10^6$ cell/ml, that concentration with PHA at 2 μg/ml is chosen as the optimal.

Preliminary experiments, in tubes rather than flasks, were performed to determine the parameters for ciprofloxacin and two other 4-aminoquinolone antibiotics (Norfloxacin and Ofloxacin) to enhance cytokine production from human leukocytes following exposure to PHA. Table III shows that 80 μl/ml of each of these 4-aminoquinolone antibiotics enhanced production of IL-1, IL-2, IL-6, IFN.gamma., TNF.alpha., and G-CSF. IL-8 production was maximal. IL-3, IL-4, and IL-7 were undetectable under these circumstances in all supernatants. These results indicate that under these serum free conditions all 4-aminoquinolones tested at 80 μg/ml enhanced PHA induced cytokine production under serum-free conditions.

TABLE II

| | PHA | Ciprofloxacin | Norfloxacin | Ofloxacin |
|---|---|---|---|---|
| | Alone & PHA | & PHA | & PHA | |
| IL-1-β | 81 | 1080 | 783 | 810 |
| IL-2 | ND | 120 | 32 | 82 |
| IL-6 | 1665 | > 3000 | > 3000 | > 3000 |
| IL-8 | 18000 | > 18000 | > 18000 | > 18000 |
| IFN.gamma. | ND | 750 | 210 | 380 |
| TNF α | 54 | 1935 | 1500 | 4000 |
| GM-CSF | 114 | 4.5 | 4.5 | 72 |
| G-CSF | 41 | 555 | 800 | 630 |

Units for cytokines other than IL2 are pg/ml and for IL2 international unit/ml.

It was also determined that a monoclonal antibody, OKT-3, (Ortho) which induces T lymphocytes to proliferate and produce interleukins could be employed as a stimulant under these conditions. Table III shows that OKT-3 induced cytokines similar to those induced by PHA plus ciprofloxacin with cells incubated in flasks as set forth in Example 1. IL-3, 4, 5 and 7 were not detected with either set of stimulants. OKT-3 produced a small additive effect for several ILs when joined with PHA and ciprofloxacin (CIPRO).

TABLE III

| | CIPRO | OKT-3 + CIPRO + PHA | OKT-3 + PHA |
|---|---|---|---|
| IL-1-β | 1080 | 1530 | 1125 |
| IL-2 | 120 | 340 | ND |
| IFN gamma. | 750 | 4660 | 11280 |
| IL-6 | > 3000 | > 3000 | 1980 |
| IL-8 | > 18000 | > 18000 | > 18000 |
| TNF alpha | 1935 | 2700 | 2500 |
| GM-CSF | 4.5 | 12 | 75 |
| G-CSF | 555 | 375 | ND |

Units of interleukins other than IL2 are pg/ml and for IL2 international units/ml. ND not done.

Figure 4:
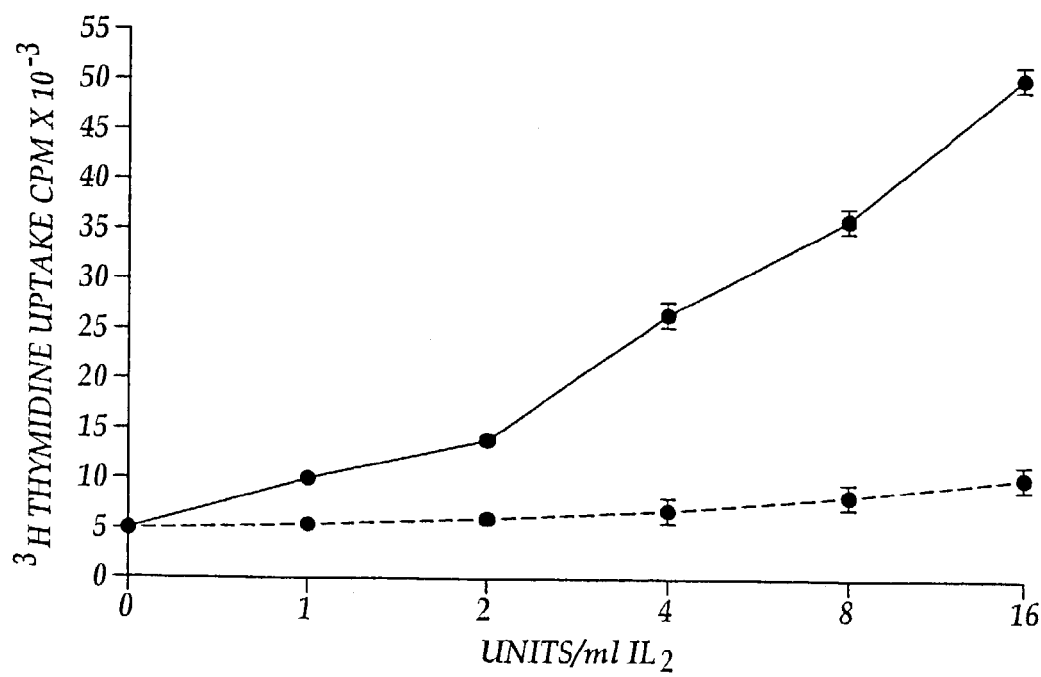
FIG. 4 is a graph of thymidine uptake versus units per ml of IL2 relating to splenocytes.
Figure 5:
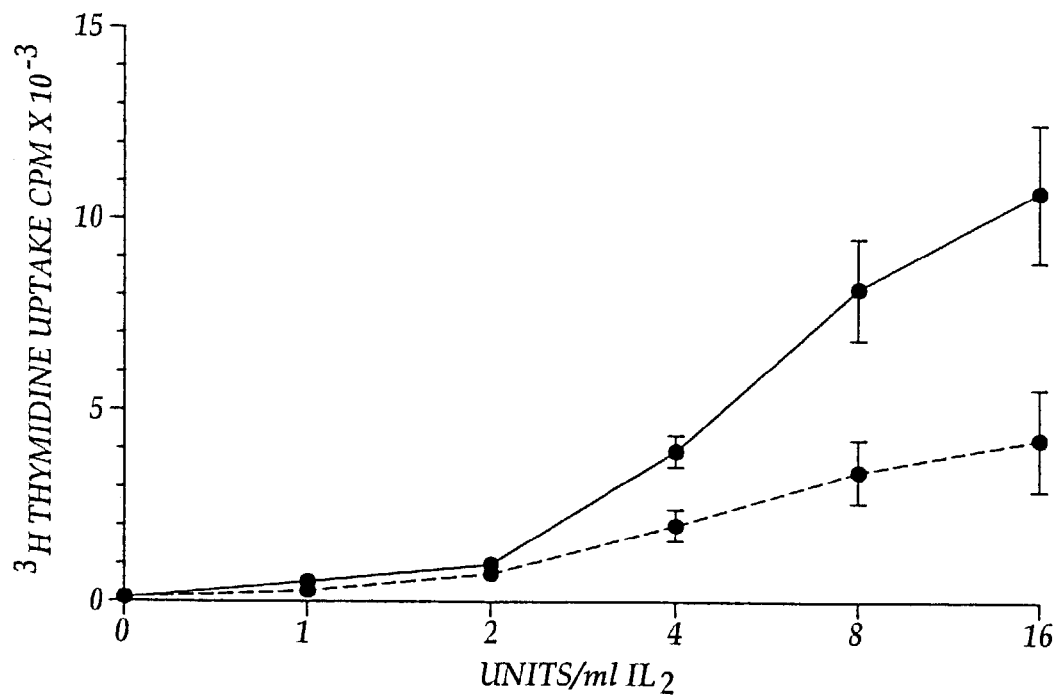
FIG. 5 is a graph similar to FIG. 2 related to thymocytes.

In order to show the superiority of the NCM over rIL-2 in vitro, mouse splenocytes and thymocytes were cultured with MEM and rIL-2 at comparable levels of IL2 as determined by bioassay and DNA synthesis measured by tritiated thymidine incorporation. NCM induces greater proliferation of splenocytes (FIG. 4) and thymocytes (FIG. 5) then rIL-2 based on IL2 content.

Figure 6:
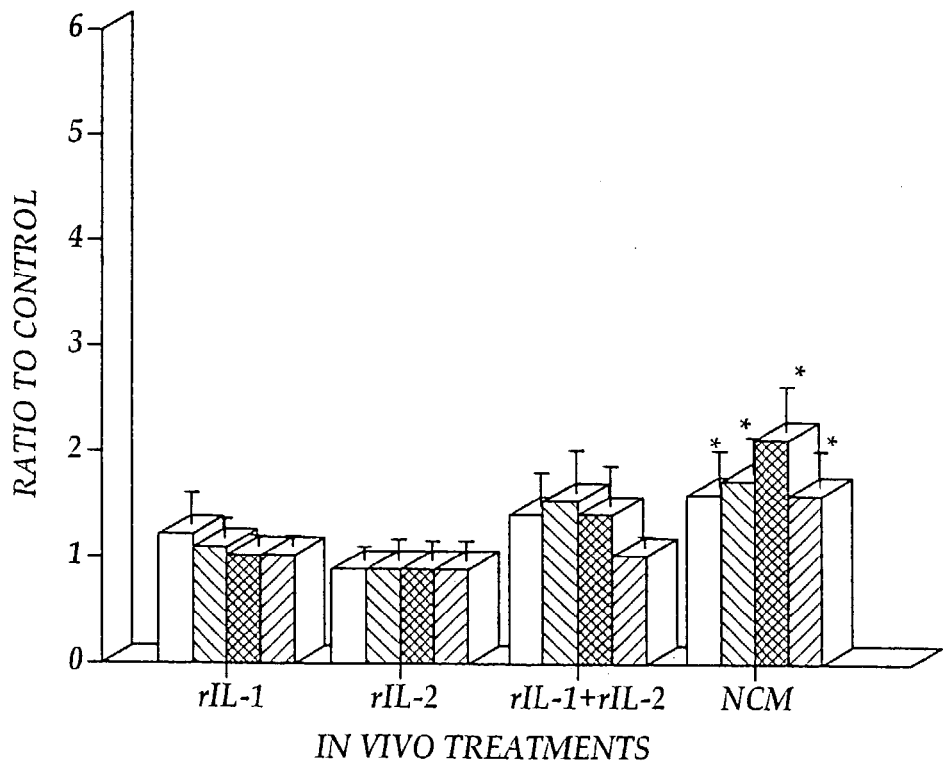
FIG. 6 is a graph showing ratio to control versus in vivo treatments for mice with involuted thymuses is treated with IL1, IL2 or IL combinations, NCM, or saline.

In a series of experiments as set forth in FIGS. 6 and 7, mice with involuted thymuses were treated in vivo with rIL-1, rIL-2, combinations of these factors, NCM or saline (controls). The spleens and thymuses were removed, the cells tested for cell proliferation responses against the interleukins (IL-1, IL-2), NCM and the mitogen ConA. The results are expressed as ratio to the saline treated control. In vivo treatment with rIL-1, rIL-2, and their combination (rIL-1 and rIL-2) had no significant effect to increase proliferative responses of splenocytes (FIG. 6) or of thymocytes (FIG. 7) to in vitro stimulation with IL-1, IL-2, NCM or ConA. NCM treatment in vivo augmented significantly both splenocytes and thymocytes to all four stimuli. These results are consistent with an enhanced sensitivity of these cells to stimulation and/or an increase in the number of responsive cells.

FIGS. 8 and 9 demonstrate the effect of NCM treatment in vivo on splenocyte and thymocyte markers. Non-mature T-cells are indicated by –– and may represent T lymphocyte precursors particularly in the thymus. NCM increased proportionately this population in spleen and thymus. Immature T-cells are indicated by ++ and this population is proportionately decreased in thymus by NCM treatment. Mature T-cells are indicated by CD4+ and CD8+. NCM increased the proportions of mature T-cells in thymus and their number in spleen. These results are consistent with an effect of NCM to increase T cell precursors and to promote their development to mature T cells in thymus.

Figure 10:
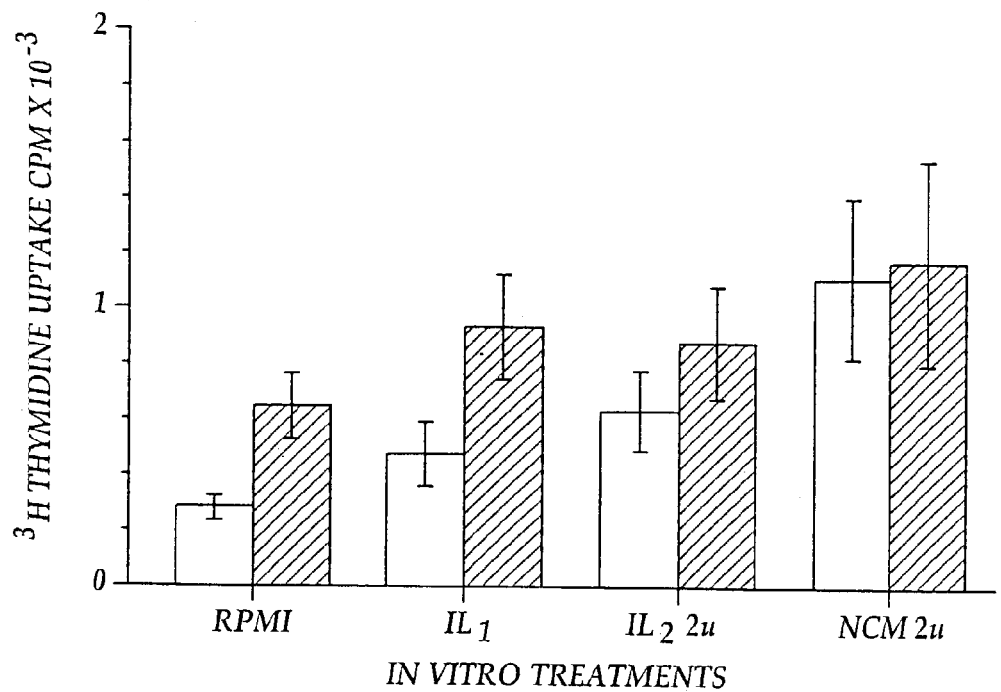
FIG. 10 is a graph demonstrating splenocyte and splenocyte responses to in vitro media including various recombinant interleukins or NCM after treatment in vivo with control media or NCM.
Figure 11:
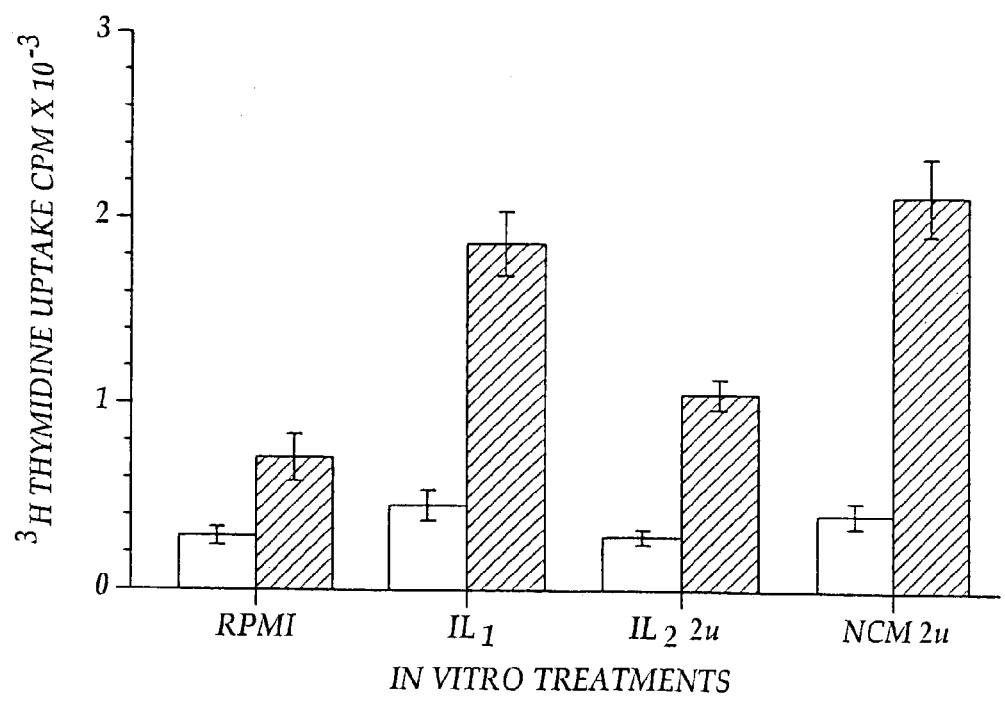
FIG. 11 is a bar graph demonstrating the splenocyte and thymocyte responses in vitro to media, various interleukins, or NCM in vivo with control media or NCM.

FIGS. 10 and 11 demonstrate the splenocyte and thymocyte responses in vitro to media (RPMI), rIL-1 (IL1), rIL-2 (IL$_2$), or NCM after treatment in vivo with control media or NCM in the hydrocortisone model. The mice were treated as described hereinabove. These data demonstrate that NCM augments background splenocyte responses, splenocyte responses to IL-1 and IL-2, but not NCM and background thymocyte responses and thymocyte responses to IL-1, IL-2, and NCM.

Figure 12:
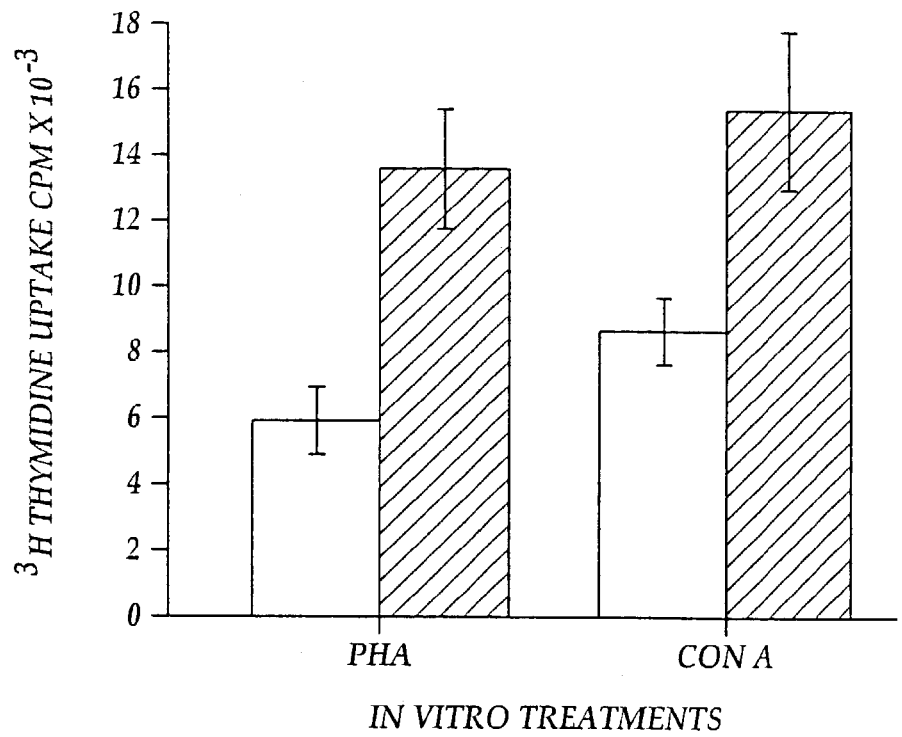
FIG. 12 demonstrates responses in splenocyte and thymocyte in vitro to ConA and PHA after treatment in vivo with control or NCM.
Figure 13:
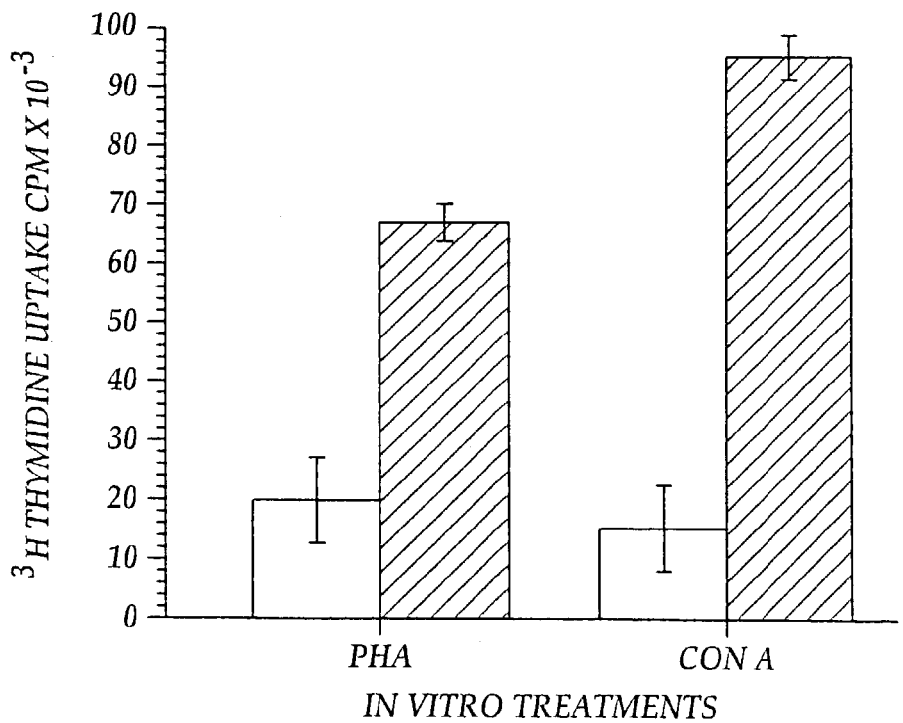
FIG. 13 demonstrates responses in splenocyte and thymocyte in vitro to ConA and PHA after treatment in vivo with control or NCM.
Figure 14:
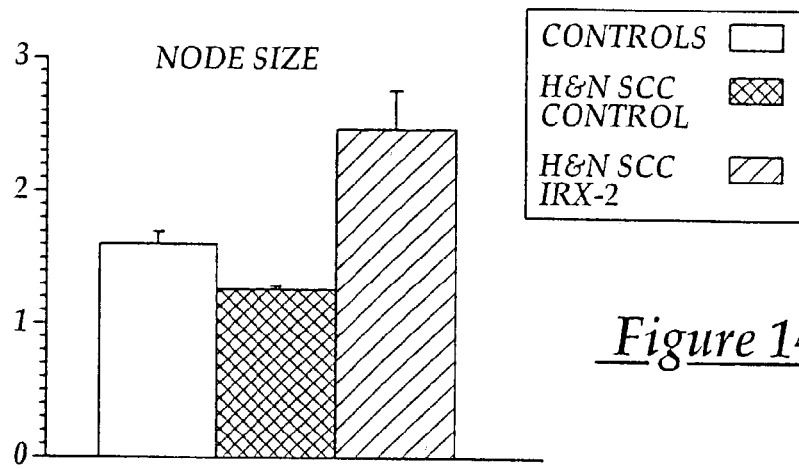
FIG. 14 is a bar graph showing node size in controls, and cancer controls or IRX-2(NCM) treated populations with squamous cell head & neck cancer (H&NSCC)
Figure 15A:
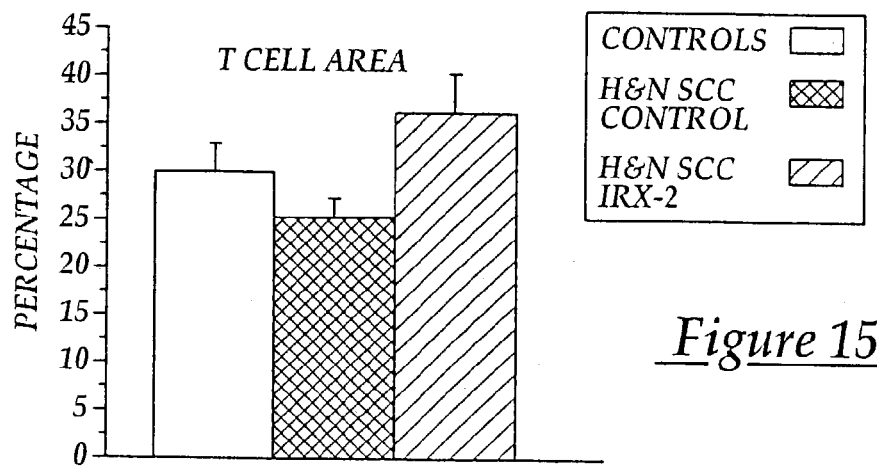
FIG. 15 shows two bar graphs, one showing T-cell area and the second showing density in controls and head and neck squamous cancer controls and patients treated with NCM(IRX-2)
Figure 15B:
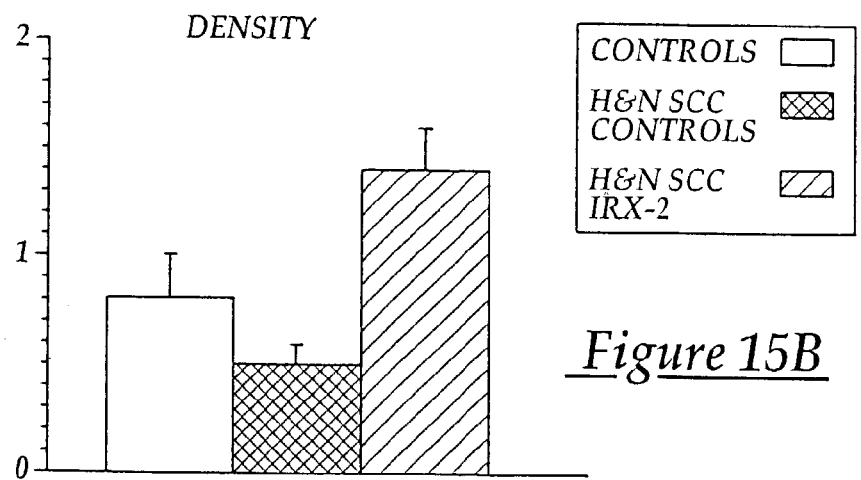
Figure 16A:
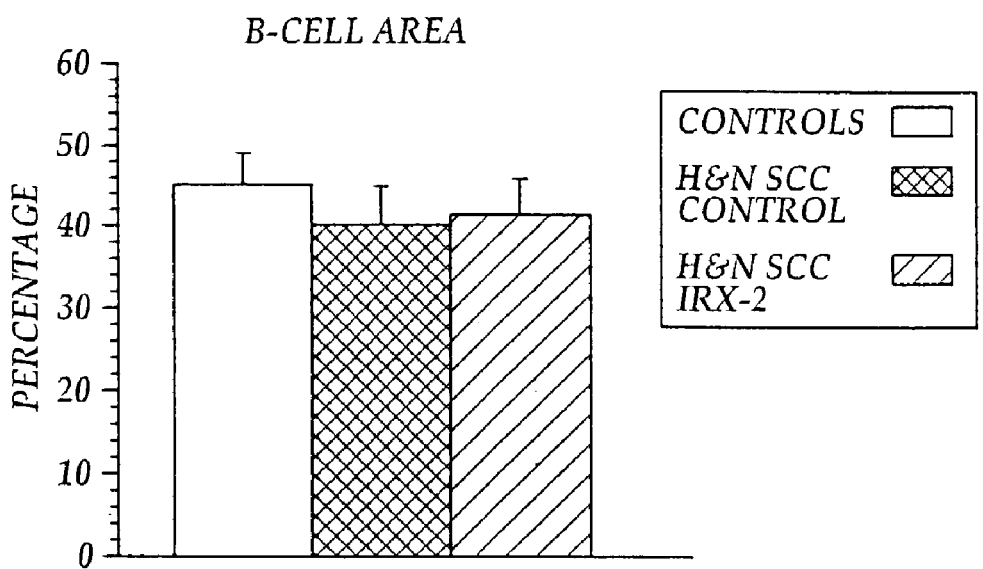
FIG. 16 shows two bar graphs showing B-cell area and follicles in the three treatment groups.
Figure 16B:
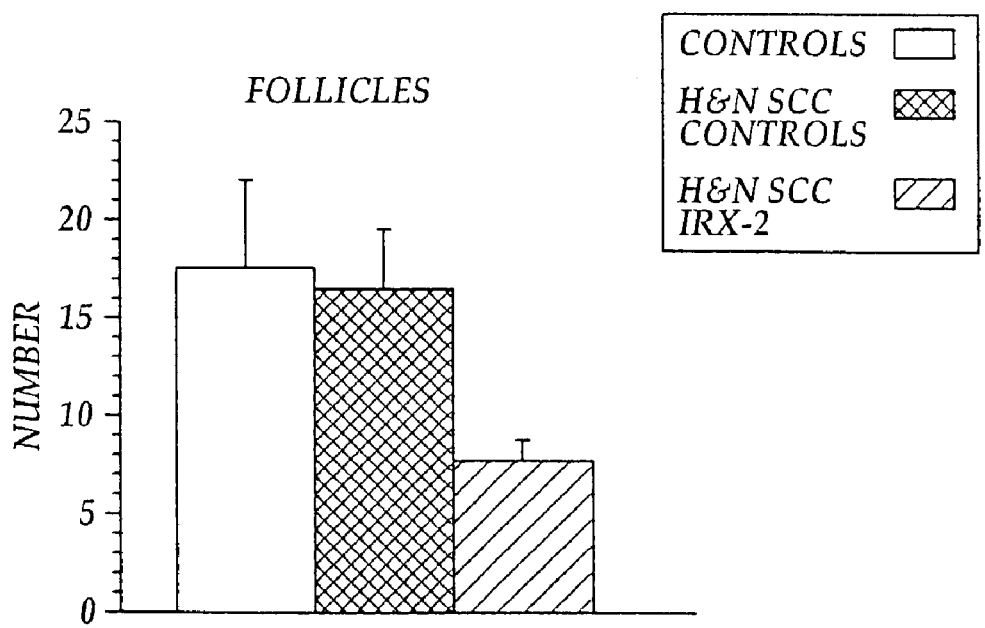
Figure 17A:
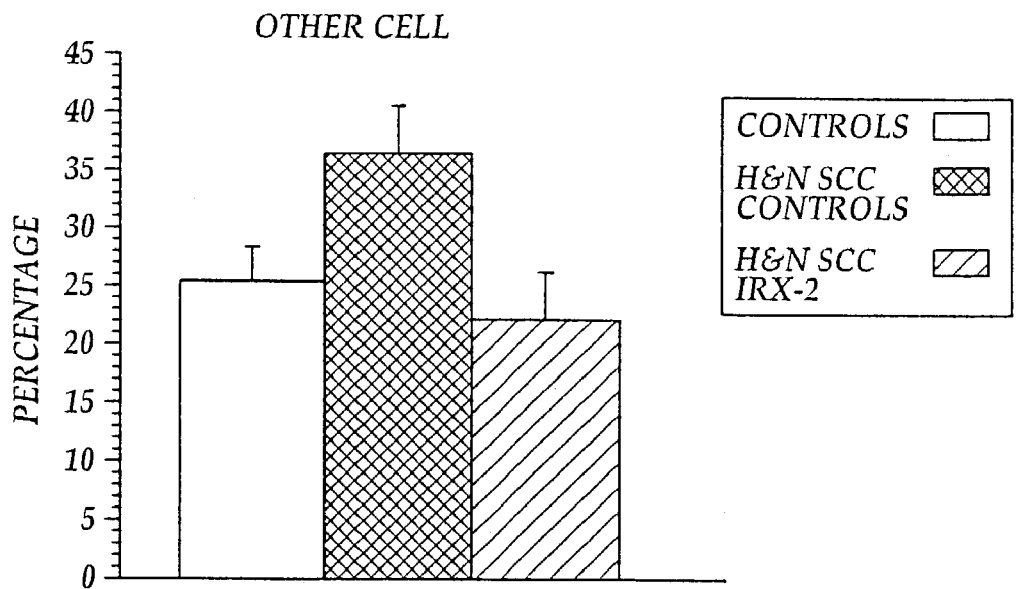
FIG. 17 shows a comparison of other cells and sinus histocytosis in the three treatment groups.
Figure 17B:
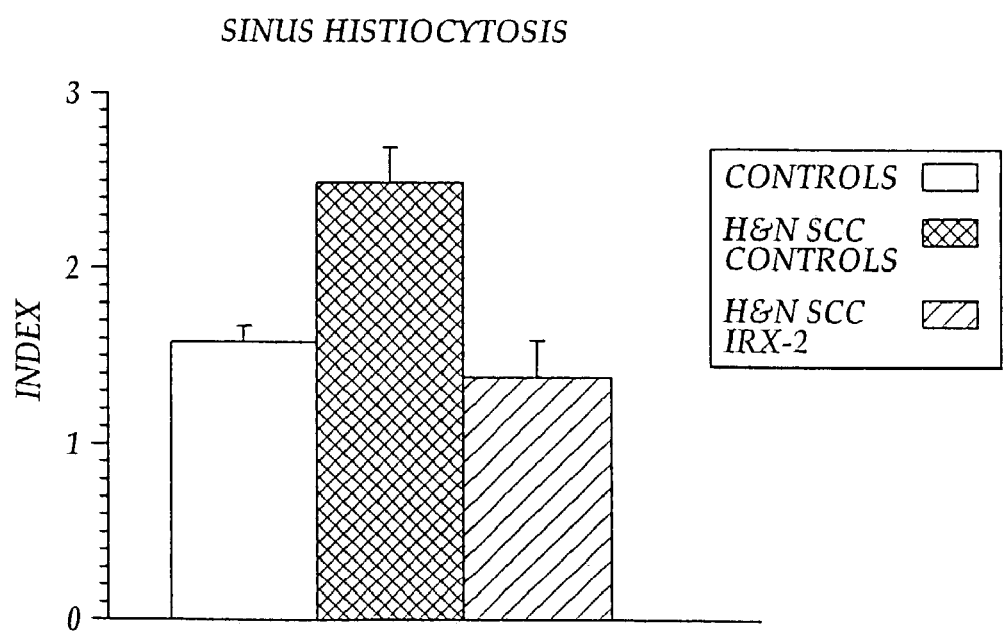
Figure 18:
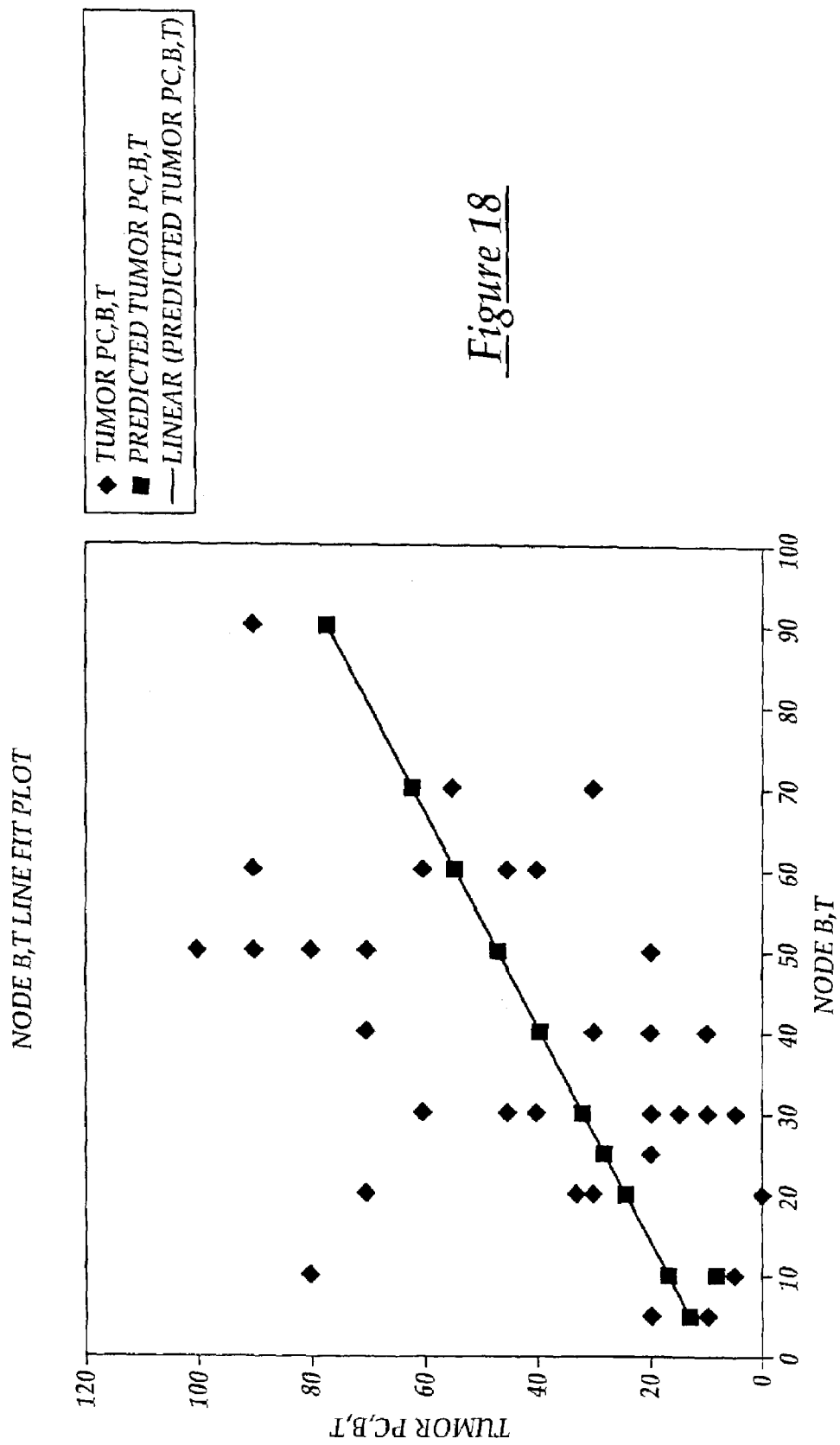
FIG. 18 is a graph showing node B&T and Cancer B&T fit plot.

FIGS. 12 and 13 demonstrate the splenocyte and thymocyte responses in vitro to ConA and PHA after treatment in vivo with control media or NCM. The mice were treated as described hereinabove.

The in vitro studies demonstrate the superiority of NCM over rIL-2 at equivalent doses in sensitizing splenocytes and thymocytes to proliferation signals. The effects on thymocytes reflect promotion of differentiation as well. The NCM composition, but not rIL-1, rIL-2, nor their combination, potently promotes in vivo T lymphocyte function (IL responses) and development (mitogen responses and cell markers) which is therapeutically relevant in any therapeutic measures requiring stimulation of the immune system or restoring even partial functioning of a damaged or defective immune system. For example chemotherapeutic agents can damage cells, including T lymphocytes, involved in the immune response. The present invention by stimulating the T lymphocyte functioning and development can restore, either partially or entirely, this feature of the immune system if damaged.

EXAMPLE 2

There is shown that local perilymphatic injections in the neck having NCM plus low dose cyclophosphamide, indomethacin, and zinc and induced clinical regressions in a high percentage of patients with squamous cell head and neck cancer (H&NSCC) (Hadden J W, et al., Arch Otolaryngol Head Neck Surg. 120:395–403, 1994; Meneses A, et al., Arch Pathol Lab Med 122:447–454, 1998; Barrera J, et al., Arch Otolaryngol Head Neck Surg 126:345–351, 2000) with evidence of improved, recurrence-free survival. Overall, including minor response (25%–50%) tumor shrinkage and reduction of tumor in pathological specimens, over 90% responded and the majority had greater than 50% tumor reduction.

These responses were speculated to be mediated by immune regression since both B and T lymphocytes were observed infiltrating the tumors. The therapy was not associated with significant toxicity.

Several unpublished observations serve to document this speculation and lead to the present invention.

1) Treatment of lymphocytopenic cancer patients with the combination of NCM has resulted in marked lymphocyte mobilization; where analyzed, these patients showed increases in CD45RA positive T-cells (i.e., naïve T cels (Table IV).

2) Intratumoral or peritumoral injection of NCM in patients with H&NSCC resulted in either reversing immunotherapy-induced tumor regression or in progression of the tumor. The tumor is thus not the site of immunization.

3) Analysis of regional lymph nodes revealed unpublished data which indicate that the regional lymph node is the site of immunization to postulated tumor antigens (see FIGS. 14–18).

4) None of these patients treated with NCM developed metastasis expected in 15% clinically and up to 50% pathologically, indicating systemic immunity rather than merely local immunity had been induced.

5) Patients were pretested with a skin test to 0.1 ml of NCM prior to treatment. More than 90% of those with a positive skin test (>0.3 mm at 24 hours) had robust clinical and pathological response. Patients with negative skin tests had weak or no response. Thus skin testing appears to select good responders.

Major increases were observed in T lymphocyte counts ($CD_2$) 752→1020 in these T lymphocytopoenic patients (T cell counts 752 vs. normal=1600). Importantly there was a corresponding increase in "naïve" CD45RA positive T cells (532→782). As mentioned previously these increases are generally not thought to occur in adults particularly with a pharmacological therapy like NCM. These cells presumably are recent thymic émigrés and could be considered a major new capacity for responding to new antigens like tumor antigens. The preexisting CD45RA positive cells were not responding to the tumor antigens and may well be incapable of doing so due to the tumor-induced immune suppression (anergy).

The literature (Hadden J W, Int'l J Immunopharmacol 11/12:629–644, 1997; Hadden J W, Int'l J Immunopharmacol 21:79–101, 1999) indicates that for both SCC and adenocarcinomas, the two major types of cancer, regional lymph nodes reflect abnormalities related to the tumor, including sinus histocytosis, lymphoid depletion and often the presence of tumor-associated lymphocytes capable of reacting to tumor cells (with IL-2). With metastasis lymphoid depletion and depressed function occur. An unpublished analysis of uninvolved cervical lymph nodes 10H&NSCC and 10 controls showed reduction in average size and an increase in sinus histocytosis associated with H&NSCC (FIGS. 14–17).

TABLE IV

Treatment of Lymphocyte Phase Patients with H&NSCC with NCM - Increases in Naive T cells in blood (#/mm³)

| PATIENT # | NAIVE T CELL MARKER | | | PAN T CELL MARKER | | |
|---|---|---|---|---|---|---|
| | PRE | POST | INCREASE | PRE | POST | INCREASE |
| 1 | 479 | 778 | +299 | 704 | 1171 | +467 |
| 2 | 938 | 1309 | +371 | 1364 | 1249 | −115 |
| 3 | 98 | 139 | +41 | 146 | 178 | +32 |
| 4 | 341 | 438 | +97 | 655 | 590 | −65 |
| 5 | 567 | 652 | +97 | 453 | 643 | +190 |
| 6 | 658 | 1058 | +400 | 1118 | 1714 | +569 |
| 7 | 642 | 1101 | +459 | 822 | 1601 | +779 |
| MEAN | 532 | 782 | +250 | 752 | 1020 | +269 |

Following treatment with one cycle of the NCM (IRX-2) protocol (Hadden J W, et al., Arch Otolaryngol Head Neck Surg. 120:395–403, 1994; Meneses A, et al., Arch Pathol Lab Med 122:447–454, 1998; Barrera J, et al., Arch Otolaryngol Head Neck Surg 126:345–351, 2000), the uninvolved cervical lymph nodes showed the changes indicated in FIGS. 14–17). Compared to the regional lymph nodes of patients with H&NSCC not treated with NCM, these nodes showed a significant increase in size, T cell area and density, and decreases in number of germinal centers and sinus histocytosis and congestion. The lymph nodes of treated patients were all stimulated and were larger than control nodes with increased T cell area and density. These nodes were thus not only restored to normal but showed evidence of T cell predominance, a known positive correlate with survival in H&NSCC (Hadden J W. Int'l J Immunopharmacol 11/12:629–644, 1997).

Importantly, when the lymph node changes related to B and T cell areas were correlated with the changes in their tumors reflecting T and B cell infiltration, a high degree of correlation was obtained for T cells (p.<0.01) and B cell s(<0.01) and overall lymphoid presence (p.<0.001). (FIG. 18) In turn, these changes correlate with tumor reduction by pathological and clinical criteria. These findings indicate that the tumor reactions are directly and positively correlated with lymph node changes and that the tumor reaction reflects the lymph node changes as the dependent variable. These findings, taken into conjunction with knowledge about how the immune system works in general (Roitt I, Brostoff J, Male D. Immunology, J B Lippincott Co, Phila, Pa., 1989), and following tumor transfection with a cytokine gene (Maass G, et al, Proc Natl Acad Sci USA, 1995, 92:5540–5542), indicate that the NCM protocol immunizes these patients to yet unidentified tumor antigens at the level of the lymph nodes. No one has previously presented evidence for lymph node changes reflecting immunization with autologous tumor antigens. These data convince the applicant that this constitutes a good starting point for trying to induce immunization with previously ineffective or poorly effective tumor antigens in an effect to yield regression of distant metastases.

EXAMPLE 3

Two patients were treated with lymphoma of the head and neck.

The patients included were those with head and neck cancer who agreed to participate in the protocol. The following scheme was followed:

Before treatment, the patients were skin-tested with NCM 0.1 ml subcutaneously in the forearm, the region was marked, and 24 hrs. later the test was read. The test was considered positive if the induction and erythema was equal or larger than 3 mm.

| Each cycle of NCM was for 21 days as follows: | |
| --- | --- |
| Day 1: | Low dose cyclophosphamide (300 mg/m$^2$i.v.) |
| Day 1–21: | Indomethacin 25 mg p.o. 3 times daily |
| | Zinc sulfate 50 mg p.o. once daily |
| Day 3–12: | NCM 200 units five as 1 ml subcutaneously perilymphatic in the neck. |

Case #1

The patient was a 23-year-old male who presented on with a prior history of three months of the presence of a tumor on the left submaxillary region, with no other symptoms. In the emergency room, he was found to have lymph adenopathy of the left submaxillary triangle, of approximately 6.5 cm in diameter of a hard consistency, partially fixed at deep levels. The rest of the physical exam was normal. The incisional biopsy showed Hodgkin's lymphoma. The lesion was staged ECIIA. A one-cycle treatment of NCM was given, obtaining a minor response, as the adenopathy reduced in size by 1 cm in diameter. The biopsy report obtained after NCM treatment showed 60% of the lesion showed normal lymphocytic infiltration, and the rest of the neoplasia (40%) showed necrosis. No viable tumor cells were found.

Following this, the patient received radiation treatment in the neck of 3600 rads. The patient is currently free of disease.

Case #2

The patient is an 82-year-old male, who presented with a two-month history of a painful mid-neck tumor mass, as well as a 10 kg loss of weight. On physical exam, the patient presented with tumor on the right palatine tonsil, which was enlarged to approximately 4×3 cm, with an ulcer in the center of the tonsil. On the neck, a right submaxillary lymph node measured approximately 2×2 cm and a lymph node mass at level II and III of approximately 5×5 cm. The rest of the exam was normal. The incisional biopsy of the tonsil and one of the neck's lymph nodes demonstrated defined non-Hodgkin's lymphoma mixed, of intermediate grade.

The patient was subjected to two cycles of NCM at the end of which a 1 cm reduction in the diameter of the tonsil and neck adenopathy was observed. The pathological report post-NCM treatment showed live tumor 20%, fragmented and necrotic 30% and normal lymphocyte infiltration 50%.

The patient was given chemotherapy (CHOP) for 6 cycles and later external radiotherapy (RT) at a total dose of 4600 rads. He recurred at eight months post RT with adenomegaly at the occipital level. The patient died three months later with evidence of neck disease.

EXAMPLE 4

Ten patients with untreated early stage cervical cancer, clinically staged IB1, IB2 and IIA were treated with local, perilymphatic injections NCM as IRX-2 (10 daily injections) followed by radical hysterectomy at day 21. One day before starting IRX2, patients received a single IV dose of cyclophosphamide at 300 mg/m$^2$. oral indomethacin or ibuprofen and zinc sulfate were administered from days 1 to 21. The clinical and pathological response, toxicity and disease-free survival were evaluated.

All patients completed NCM treatment and were evaluated for response and toxicity. Clinical response was seen in 50% of patients (3 partial response (PR), 2 minor response (MR) (>25%<50%reduction)). Seven patients underwent surgery, Pathologically tumor reduction associated with tumor fragmentation was found in five cases. There was a rather heterogeneous pattern of cell types infiltrating the tumor which included lymphocytes, plasma cells, neutrophils, macrophages and eosinophils. Treatment was well-tolerated except for mild pain and minor bleeding during injection and gastric intolerance to indomethacin. At a 24 months of follow-up, nine patients are disease-free.

This previously unpublished study shows that peritumoral NCM induces immune-mediated tumor response in early stage untreated cervical carcinoma.

EXAMPLE 5

Two patients with liver metastasis from primary hepatocellular carcinoma were treated with intrasplenic NCM (1 or 3 injections). The protocol was otherwise as previously described for the H&NSCC, cervical, or lymphoma cases. One patient with advanced hepatocellular carcinoma had a partial response confirmed by tomography, no histology is available. The other had a partial response confirmed by surgery. Histological exam showed tumor reduction, fragmentation, and lymphorid infiltration.

EXAMPLE 6

Four patients with squamous cell carcinoma of the penis (human papiloma virus associated) were treated with the NCM protocol as described above; all four had partial responses clinically and the surgical specimen showed tumor reduction and fragmentation and lymphoid infiltration characteristic of the H&NSCC cancer patients.

EXAMPLE 7

Mice were immunized with PMSA peptides conjugated to ovalbumen 100 µg at 3 sites (day 1, 14, and 21) with alum (1:1 Vol) as adjuvant (5@) or NCM (20 units IL2 equivalence) (5@) animals were skin tested at day 28 with ovalbumen (100 µg) (2@) or peptides (100 µg) (3@). Two animals treated with ovalbumen plus NCM without peptides responded to ovalbumen with positive skin tests. Two animals treated with ovalbumen plus alum did not respond. 2 of 3 animals treated with ovalbumen plus peptides and NCM responded. None of the animals treated with ovalbumen plus peptides and alum responded. Thus NCM was a superior adjuvant to alum for both tumor peptides and ovalbumen as antigens.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

REFERENCES

U.S. Pat. No. 4,116,951
U.S. Pat. No. 4,353,821
U.S. Pat. No. 4,390,623
U.S. Pat. No. 4,439,196
U.S. Pat. No. 4,447,224
U.S. Pat. No. 4,447,233
U.S. Pat. No. 4,464,355
U.S. Pat. No. 4,466,918
U.S. Pat. No. 4,470,926
U.S. Pat. No. 4,475,196
U.S. Pat. No. 4,486,194
U.S. Pat. No. 4,487,603
U.S. Pat. No. 4,612,365
U.S. Pat. No. 4,910,296
U.S. Pat. No. 4,925,678
U.S. Pat. No. 4,959,217
U.S. Pat. No. 5,100,664
U.S. Pat. No. 5,167,616
U.S. Pat. No. 5,169,383
U.S. Pat. No. 5,225,182
U.S. Pat. No. 5,503,841
U.S. Pat. No. 5,632,983
U.S. Pat. No. 5,643,565
U.S. Pat. No. 5,698,194
U.S. Pat. No. 5,800,810
U.S. Pat. No. 6,060,068

Publications

Albert et al, Nature, Vol. 392, pp.86–89 (1998)
Banchereau et al, Annual Reviews of Immunology, (2000), Vol. 18, pp. 767–811
Barrera J, Verastegui E, Meneses A, Zinser J, de la Garza J, Hadden J W. Combination immunotherapy of squamous cell head and neck cancer: A phase II trial. Arch Otolaryngol Head Neck Surg 126:345–351, 2000.
Bellone, et al, Immunology Today, Vol 20, No. 10, p 457–462, 1999
Berd D, Mastrangelo M J. Effect of low dose cyclophosphamide on the immune system of cancer patients: reduction of T suppressor function without depletion of the CD8+subset. Cancer Research 47:3317–3321, 1987.
Berd D. Low doses of chemotherapy to inhibit suppressor T cells. Progress in Clin Biol Res 288:449–458, 1989.
Borysiewickz L K, Fiander A. Nimako M. A recombinant vaccine virus encoding human papilomavirus type 16 and 18, E6 and E7 proteins as immunotherapy for cervical cancer. Lancet 347:1524–1527, 1996.
Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251–270 (1991).
Capecchi, "Altering the genome by homologous recombination" *Science* 244:1288–1292 (1989).
Cortesina G, DeStefani A, Galcazzi E. Temporary regression of recurrent squamous cell carcinoma of the head and neck is achieved with a low dose but not a high dose of recombinant interleukin 2 injected perilymphatically. Br J Cancer 69:572–577, 1994.
Cortesina G, DeStefani A, Giovarelli M, et al. Treatment of recurrent squamous cell carcinoma of the head and neck with low doses of interleukin-2 injected perilymphatically. Cancer 62:2482–2485, 1988.
Cregg J M, Vedvick T S, Raschke W C: Recent Advances in the Expression of Foreign Genes in *Pichia pastoris*, Bio/Technology 11:905–910, 1993.
Culver, 1998. Site-Directed recombination for repair of mutations in the human ADA gene. (Abstract) Antisense DNA & RNA based therapeutics, February, 1998, Coronado, Calif.
Davies et al., "Targeted alterations in yeast artificial chromosomes for inter-species gene transfer", *Nucleic Acids Research*, Vol. 20, No. 11, pp. 2693–2698 (1992).
Deans et al., 1989
DeLaugh and Lotts, Current Opinion In Immunology, 2000, Vol. 12, pp. 583–588.
Dickinson et al., "High frequency gene targeting using insertional vectors", *Human Molecular Genetics*, Vol. 2, No. 8, pp. 1299–1302 (1993).
Duff and Lincoln, "Insertion of a pathogenic mutation into a yeast artificial chromosome containing the human APP gene and expression in ES cells", *Research Advances in Alzheimer's Disease and Related Disorders*, 1995.
Gilboa, E, Eglitis, M A, Kantoff, P W, Anderson, W F: Transfer and expression of cloned genes using retroviral vectors. BioTechniques 4(6):504–512, 1986.
Gillis et al., 1978
Hadden et al., 1992
Hadden et al., 1994
Hadden J W, Endicott J, Baekey P, Skipper P, Hadden E M. Interleukins and contrasuppression induce immune regression of head and neck cancer. Arch Otolaryngol Head Neck Surg. 120:395–403, 1994.
Hadden J W, Saha A R, Sosa M, Hadden E M. Immunotherapy with natural interleukins and/or Thymosin $\alpha_1$ potently augments T lymphocyte responses of hydrocortisone-treated aged mice. Int'l J Immunopharmacol 17:821–828. 1995.
Hadden J W. Immunology and immunotherapy of breast cancer: An update: Int'l J Immunopharmacol 21:79–101, 1999.
Hadden J W. The immunopharmacology of head and neck cancer: An update. Int'l J Immunopharmacol 11/12: 629–644, 1997.
Hadden J W. The treatment of zinc deficiency is an immunotherapy. Int'l J Immunopharmacol 17:696–701, 1995.
Hank A J, Albertini M R, Sondel P M. Monoclonal antibodies, cytokines and fusion proteins in the treatment of malignant disease. Cancer Chemother & Biol Resp Mod 18:210–222, 1999.
Huston et al, 1991 "Protein engineering of single-chain Fv analogs and fusion proteins" in Methods in Enzymology (J J Langone, ed.; Academic Press, New York, N.Y.) 203:46–88.
Huxley et al., "The human HPRT gene on a yeast artificial chromosome is functional when transferred to mouse cells by cell fusion", *Genomics*, 9:742–750 (1991).
Jakobovits et al., "Germ-line transmission and expression of a human-derived yeast artificial chromosome", *Nature*, Vol. 362, pp. 255–261 (1993).
Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203: 88–99.
June et al., 1989

Kavanaugh D Y, Carbone D P. Immunologic dysfunction in cancer. Hematol-Oncol Clinics of North Amer 10(4): 927–951, 1996.

Lamb et al., "Introduction and expression of the 400 kilobase precursor amyloid protein gene in transgenic mice", *Nature Genetics*, Vol. 5, pp. 22–29 (1993).

Maass G, Schmidt W, Berger M, et al. Priming of tumor-specific T-cells in the draining lymph nodes after immunization with interleukin 2-secreting tumor cells: three consecutive stages may be required for successful tumor vaccination. Proc Natl Acad Sci USA, 1995, 92:5540–5542.

Mackall (Stem Cells 2000, Vol. 18. pp. 10–18)

Mackall et al, (New England Journal of Medicine (1995), Vol. 332, pp. 143–149)

Maclean G D, Miles D W, Rubens R D, Reddish M A, Longenecker bone marrow. Enhancing the effect of Theratope STn-KLH cancer vaccine in patients with metastatic breast cancer by pretreatment with low-dose intravenous cyclophosphamide. J Immunother Emphasis Tumor Immunol 19(4):309–316, 1996.

Marshak et al, "Strategies for Protein Purification and Characterization. A laboratory course manual." CSHL Press, 1996

Mastrangelo M J, Maguire H C Jr., Sato T, Nathan F E, Berd D. Active specific immunization in the treatment of patients with melanoma. (Review) Seminars in Oncology 23(6):773–781, 1996.

Meneses A, Verastegui E, Barrera J L, Zinser J, de la Garza J, Hadden J W. Histological findings in patients with head and neck squamous cell carcinoma receiving perilympatic natural cytokine mixture prior to surgery. Arch Pathol Lab Med 122:447–454, 1998.

Mernaugh and Mernaugh, 1995 "An overview of phage-displayed recombinant antibodies" in Molecular Methods In Plant Pathology (R P Singh and U S Singh, eds.; CRC Press Inc., Boca Raton, Fla.) pp. 359–365.

Mishell and Shiigi (Selected Methods in Cellular Immunology, 1981)

Murphy G P, Tjoa B A, Simmons S J. The prostate. 38:43–78, 1999.

Pearson and Choi, *Expression of the human b-amyloid precursor protein gene from a yeast artificial chromosome in transgenic mice*. Proc. Natl. Acad. Sci. USA, 1993. 90:10578–82.

Riesenbeck et al., 1994

Roitt I, Brostoff J, Male D. Immunology, J B Lippincott Co, Phila, Pa., 1989.

Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281–301 (1991).

Saha A, Hadden E M, Hadden J W. Zinc induces thymulin secretion from human thymic epithelial cells in vitro and augments splenocytes and thymocyte response in vivo. Int'l J Immunopharmacol 17:729–734, 1995.

Sahin U, Tureci O, Pfreundschuh. Serological identification of human tumor antigens. Curr Opin Immunol 9:709–715, 1997.

Sanda M G, Smith D C, Charles L G. Recombinant vaccinia-PSA (Prostvac) can include a prostate-specific immune response in androgen-modulated human prostate cancer. Urology 52:2, 1999.

Schedl et al., "A yeast artificial chromosome covering the tyrosinase gene confers copy number-dependent expression in transgenic mice", *Nature*, Vol. 362, pp. 258–261 (1993).

Sprent, et al, Science, Vol 293, Jul. 13, 2001, pgs 245–248

Strauss et al., "Germ line transmission of a yeast artificial chromosome spanning the murine $a_1$ (I) collagen locus", *Science*, Vol. 259, pp. 1904–1907 (1993).

Tagawa M. Cytokine therapy for cancer. Current Pharmaceut Design 6(6):681–699, 2000.

Valente G, DeStefani A, Jemma C, Giovarelli M, Geuna N, Cortesina G, Formi G, Palestro G. Infiltrating leukocyte populations and T-lymphocyte subsets in head and neck squamous cell carcinomas from patients receiving perilymphatic injections of recombinant interleukin-2. A pathologic and immunophenotypic study. Modern Pathol 3(6):702–708, 1990.

Van der Eynde B, Van der Brugger. T cell defined tumor antigens. Curr Opin Immunol 9:684–693, 1997.

Verastegui E, Barrera J L, Zinzer J, del Rio R, Meneses A, de la Garza J, Hadden J W. A natural cytokine mixture (IRX-2) and interference with immune suppression induce immune mobilization and regression of head and neck cancer. Int'l J Immunopharmacol 11/12:619–627, 1997.

Verastegui et al, 1999

Wang R F, Rosenberg S A. Human tumor antigens for cancer vaccine development. Immunologic Reviews 170:85–100, 1999.

Webb et al. 1973

Weber J. Tumor vaccines. Medscape Anthology 3:2, 2000.

Whiteside, et al, Cancer Res. 53:5654–5662, (1993)

Wolf et al, Arch. Oto. Laryngol. 111:716–725, 1985

The invention claimed is:

1. A formulation consisting of 150–600 units of IL-2, a non-steroidal anti-inflammatory drug (NSAID) and cyclophosphamide.

2. A formulation consisting of IL-1, IL-2, IL-6, IL-8, IFN-γ and TNF-α.

* * * * *